(12) United States Patent
Li et al.

(10) Patent No.: US 8,900,575 B2
(45) Date of Patent: Dec. 2, 2014

(54) COMPOSITIONS AND METHODS FOR OXALATE REDUCTION

(75) Inventors: Qingshan Li, Gainesville, FL (US); Harmeet Sidhu, Gainesville, FL (US)

(73) Assignee: Oxthera Intellectual Property AB, Uppsala (SE)

( * ) Notice: Subject to any disclaimer, the term of this patent is extended or adjusted under 35 U.S.C. 154(b) by 847 days.

(21) Appl. No.: 11/640,126

(22) Filed: Dec. 15, 2006

(65) Prior Publication Data

US 2007/0184118 A1  Aug. 9, 2007

Related U.S. Application Data

(60) Provisional application No. 60/750,896, filed on Dec. 16, 2005.

(51) Int. Cl.
| | |
|---|---|
| *A61K 38/44* | (2006.01) |
| *A61K 9/14* | (2006.01) |
| *A61K 9/36* | (2006.01) |
| *A61K 9/32* | (2006.01) |
| *A61K 9/48* | (2006.01) |
| *A61K 9/50* | (2006.01) |
| *A61K 38/45* | (2006.01) |
| *A61K 9/16* | (2006.01) |
| *A61K 38/51* | (2006.01) |
| *A61K 38/48* | (2006.01) |
| *A61K 9/51* | (2006.01) |

(52) U.S. Cl.
CPC ......... *A61K 38/44* (2013.01); *C12Y 304/23002* (2013.01); *A61K 9/5073* (2013.01); *A61K 38/45* (2013.01); *A61K 9/1652* (2013.01); *A61K 9/5115* (2013.01); *C12Y 208/03016* (2013.01); *C12Y 401/01002* (2013.01); *A61K 38/51* (2013.01); *A61K 9/5161* (2013.01); *A61K 9/5089* (2013.01); *A61K 9/5036* (2013.01); *A61K 38/488* (2013.01); *A61K 9/5192* (2013.01); *C12Y 401/01008* (2013.01); *C12Y 102/03004* (2013.01)
USPC .......... 424/94.4; 424/489; 424/479; 424/482; 424/490; 424/463

(58) Field of Classification Search
CPC ........ C12N 11/02; C12N 11/10; C12N 11/12; C12N 11/04; C12N 9/96; C12N 9/14; C12N 15/00; A61K 38/46
See application file for complete search history.

(56) References Cited

U.S. PATENT DOCUMENTS

| | | | |
|---|---|---|---|
| 4,205,132 A | 5/1980 | Sandine et al. | |
| 4,539,118 A | 9/1985 | Crider | |
| 4,619,897 A | 10/1986 | Hato et al. | |
| 5,206,219 A | 4/1993 | Desai | |
| 5,263,992 A | 11/1993 | Guire | |
| 5,286,495 A | 2/1994 | Batich et al. | |
| 5,427,935 A * | 6/1995 | Wang et al. | .......... 435/178 |
| 5,547,870 A | 8/1996 | Datta et al. | |
| 5,554,147 A | 9/1996 | Batich et al. | |
| 5,603,971 A | 2/1997 | Porzio et al. | |
| 5,604,111 A | 2/1997 | Peck | |
| 5,607,417 A | 3/1997 | Batich et al. | |
| 5,788,687 A | 8/1998 | Batich et al. | |
| 5,868,720 A | 2/1999 | Van Antwerp | |
| 5,912,125 A | 6/1999 | Peck et al. | |
| 6,033,719 A | 3/2000 | Keogh | |
| 6,080,404 A | 6/2000 | Branham et al. | |
| 6,090,628 A | 7/2000 | Peck et al. | |
| 6,177,478 B1 | 1/2001 | Holmes-Farley et al. | |
| 6,200,562 B1 | 3/2001 | Allison et al. | |
| 6,203,797 B1 | 3/2001 | Perry | |
| 6,214,980 B1 | 4/2001 | Peck et al. | |
| 6,242,230 B1 | 6/2001 | Batich et al. | |
| 6,281,252 B1 | 8/2001 | Holmes-Farley et al. | |
| 6,297,425 B1 | 10/2001 | Schelonge et al. | |
| 6,355,242 B1 | 3/2002 | Allison et al. | |
| 6,566,407 B2 | 5/2003 | Holmes-Farley et al. | |
| 6,699,469 B2 | 3/2004 | Allison et al. | |
| 6,929,940 B1 | 8/2005 | Richards et al. | |
| 8,431,122 B2 | 4/2013 | Sidhu et al. | |
| 8,486,389 B2 | 7/2013 | Allison et al. | |
| 8,545,836 B2 | 10/2013 | Sidhu et al. | |
| 2001/0036473 A1 | 11/2001 | Scott et al. | |

(Continued)

FOREIGN PATENT DOCUMENTS

| | | |
|---|---|---|
| DE | 3030185 | 4/1982 |
| DE | 3204284 | 8/1983 |

(Continued)

OTHER PUBLICATIONS

International Search Report and Written Opinion for PCT Application No. PCT/US2005/016080 dated May 21, 2007.
Allison, M.J. et al., "Oxalate Degradation by Microbes of the Large Bowel of Herbivores: The Effect of Dietary Oxalate", Science, vol. 212, pp. 675-676, 1981.
Allison, M.J. et al., "*Oxalobacter formigenes* Gen. Nov., Sp. Nov.: Oxalate-Degrading Anaerobes that Inhibit the Gastrointestinal Tract", Archives Microbiology, vol. 141, pp. 1-7, pgs. Feb. 1985.
Allison, M.J. et al., "Oxalate Degradation by Gastrointestinal Bacteria from Humans", Journal of Nutrition, vol. 116, pp. 455-460, 1986.

(Continued)

*Primary Examiner* — Taeyoon Kim
*Assistant Examiner* — Srikanth Patury
(74) *Attorney, Agent, or Firm* — Foley & Lardner LLP

(57) ABSTRACT

The present invention comprises methods and compositions for the reduction of oxalate in humans. For example, the invention provides methods and compositions for the delivery of one or more oxalate-reducing enzymes embedded in particle compositions. The compositions of the present invention are suitable in methods of treatment or prevention of oxalate-related conditions including, but not limited to, hyperoxaluria, absorptive hyperoxaluria, enteric hyperoxaluria, primary hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and patients who have undergone gastrointestinal surgery and bariatric surgery (surgery for obesity), and/or who have undergone antibiotic treatment.

18 Claims, 8 Drawing Sheets

(56) References Cited

U.S. PATENT DOCUMENTS

| | | | |
|---|---|---|---|
| 2002/0061292 | A1 | 5/2002 | De Simone |
| 2003/0138415 | A1 | 7/2003 | Shepard |
| 2004/0120941 | A1 | 6/2004 | Allison et al. |
| 2004/0234514 | A1 | 11/2004 | Sidhu |
| 2007/0178070 | A1 | 8/2007 | Kaul et al. |
| 2007/0184118 | A1 | 8/2007 | Li et al. |
| 2008/0317810 | A1* | 12/2008 | Sidhu et al. ............ 424/423 |
| 2010/0028422 | A1 | 2/2010 | Kaul et al. |
| 2011/0002906 | A1 | 1/2011 | Sidhu et al. |
| 2013/0216515 | A1 | 8/2013 | Sidhu et al. |

FOREIGN PATENT DOCUMENTS

| | | |
|---|---|---|
| JP | 9503951 | 4/1997 |
| WO | WO 95/31537 | 11/1995 |
| WO | WO 95/35377 | 12/1995 |
| WO | WO 98/07922 | 2/1998 |
| WO | WO 98/16632 | 4/1998 |
| WO | WO 98/52586 | 11/1998 |
| WO | WO 00/21504 | 4/2000 |
| WO | WO 00/74657 | 12/2000 |
| WO | WO 02/058712 A2 | 8/2002 |
| WO | WO 2005/060937 A1 | 7/2005 |
| WO | WO 2005/123116 A2 | 12/2005 |
| WO | WO 2008/105911 A2 | 9/2008 |

OTHER PUBLICATIONS

Allison, M.J. et al., "Oxalate-Degrading Bacteria", In Khan, S.R., Calcium Oxalate in Biological Systems CRC Press, Chapter 7, pp. 131-168, 1995.

Bowersock, T.L. et al., "Oral Vaccination of Animals with Antigens Encapsulated in Alginate Microspheres", Vaccine, vol. 17, pp. 1804-1811, 1999.

Chandran, P. et al., "Improved Determination of Urinary Oxalate with Alkyamine Glass Bound Barley Oxalate Oxidase", Journal of Biotechnology, vol. 85, pp. 1-5, Jan. 2001.

Cho, N.H. et al., "Novel Mucosal Immunization with Polysaccharide-Protein Conjugates Entrapped in Alginate Microspheres", Journal of Controlled Release, vol. 53, pp. 215-224, Apr. 1998.

Daniel, S.L. et al., "Microbial Degradation of Oxalate in the Gastrointestinal Tracts of Rats", Applied and Environment Microbiology, vol. 53, No. 8., pp. 1793-1797, 1987.

Daniel, S.L. et al., "Intestinal Colonisation of Laboratory Rats by Anaerobic Oxalate-Degrading Bacteria: Effects on the Urinary and Faecal Excretion of Dietary Oxalate", Microbial Ecology in Health and Disease, vol. 6, pp. 277-283, 1993.

Dawson, K.A. et al., "Isolation and Some Characteristics of Anaerobic Oxalate-Degrading Bacteria from the Rumen", Applied and Environmental Microbiology, vol. 40, No. 4, pp. 833-839, 1980.

Defife, K.M. et al., "Effects of Photochemically Immobilized Polymer Coatings on Protein Adsorption, Cell Adhesion, and the Foreign Body Reaction to Silicone Rubber", Journal of Biomedical Materials Research, vol. 44, pp. 298-307, Mar. 1999.

Denstedt, J.D. et al., "Biomaterials Used in Urology: Current Issues of Biocompatibility, Infection, and Encrustation", Journal of Endourology, vol. 12, pp. 493-500, Dec. 1998.

Denstedt, J.D. et al., "Advances in Ureteral Stent Technology", The World Journal of Urology, vol. 18, pp. 237-242, Sep. 2000.

Ditizio, V. et al., "A Liposomal Hydrogel for the Prevention of Bacterial Adhesion to Catheters", Biomaterials, vol. 19, pp. 1877-1884, Oct. 1998.

Doane, L.T. et al., "Microbial Oxalate Degradation: Effects on Oxalate and Calcium Balance in Humans", Nutrition Research, vol. 9, pp. 957-964, 1989.

D'Urso, E.M. et al., "Poly(Ethylene Glycol)-Serum Albumin Hydrogel as Matrix for Enzyme Immobilization: Biomedical Applications", Artificial Cells, Blood Substitutes and Immobilization, Biotechnology, vol. 23, pp. 587-595, Feb. 1995.

El-Faqih et al., "Polyurethane Internal Ureteral Stents in Treatment of Stone Patients: Morbidity Related to Indwelling Times", The Journal of Urology, vol. 146, pp. 1487-1491, Dec. 1991.

Fuse, H et al., "Crystal Adherence to Urinary Catheter Materials in Rats", The Journal of Urology, vol. 151, pp. 1703-1706, Jun. 1994.

Gaboury, S.R. et al., "Analysis of Gas Plasma-Modified Poly(dimethylsiloxane) Elastomer Surfaces", American Chemical Society, pp. 777-790, 1993.

Gilchrist, T. et al., "Controlled Silver-Releasing Polymers and their Potential for Urinary Tract Infection Control", Biomaterials, vol. 12, pp. 76-78, Jan. 1991.

Han, J.Z. et al., "The Relationship of Oxalobacter Formigenes and Calcium Oxalate Calculi", Journal of Tongji Medical University, vol. 15, No. 4, pp. 249-252, 1995.

Hsiue, G.H. et al., "Surface Characterization and Biological Properties Study of Silicone Rubber Membrane Grafted with Phospholipid as Biomaterial via Plasma Induced Graft Copolymerization", J Biomed Materials Research, vol. 42, pp. 134-147 Oct. 1998.

Ito, H. et al., "A New Oxalate-Degrading Organism Isolated from Human Feces", Abstract, ASM General Meeting, Annual Meeting American Soc. Microbiol, vol. 1, p. Q-106, 1995.

Jensen, N.S. et al., "Studies on the Diversity Among Anaerobic Oxalate Degrading Bacteria Now in the Species *Oxalobacter formigenes*", Abstract, Annual Meeting American Soc. Microbiol, vol. 1, p. I-12, 1994.

Johnson, J.R. et al., "Prevention of Catheter-Associated Urinary Tract Infection with a Silver Oxide-Coated Urinary Catheter: Clinical and Microbiologic Correlates", Journal of Infectious Disease, vol. 162, pp. 1145-1150, Nov. 1990.

Keane, P.F. et al., "Characterization of Biofilm and Encrustation on Ureteric Stents in Vivo", British Journal of Urology, vol. 73, pp. 687-691, Jun. 1994.

Kulik E. et al., "In Vitro Platelet Adhesion to Nonionic and Ionic Hydrogels with Different Water Contents", Journal of Biomedical Materials Research, vol. 30, pp. 295-304, Mar. 1996.

Ko, Y.G. et al., "Immobilization of Poly (Ethylene Glycol) or its Sulfonate onto Polymer Surfaces by Ozone Oxidation", Biomaterials, vol. 22, pp. 2115-2123, Aug. 2001.

Langefeld, S. et al., "Functionally Adapted Surfaces on a Silicone Keratoprosthesis", The International Journal of Artificial Organs, vol. 22, pp. 235-241, 1999.

Lee, S.D. et al., "Characterization of Plasma-Induced Graft Polymerization of 2-Hydroxyethyl Methacrylate onto Silicone Rubber", Journal of Applied Polymer Science, vol. 54, pp. 1279-1287, 1994.

Lee, S.D. et al., "Plasma-Induced Grafted Polymerization of Acrylic Acid and Subsequent Grafting of Collagen onto Polymer Film as Biomaterials", Biomaterials, vol. 17, pp. 1599-1608, Aug. 1996.

Lee, S.D. et al., "Preparation and Characterization of a Homobifunctional Silicone Rubber Membrane Grafted with Acrylic Acid via Plasma-Induced Graft Copolymerization", Journal of Polymer Science: Part A: Polymer Chemistry, vol. 34, pp. 141-148, 1996.

Lung, H.Y. et al., "Cloning and Expression of the Oxalyl-CoA Decarboxylase Gene from the Bacterium, *Oxalobacter formigenes*: Prospects for Gene Therapy to Control Ca-Oxalate Kidney Stone Formation", Amer. J of Kidney Disease, vol. 17, pp. 381-385, 1991.

Mason, M. et al., "Attachment of Hyaluronic Acid to Polypropylene, Polystyrene, and Polytetrafluoroethylene", Biomaterials, vol. 21, pp. 31-36, Jan. 2000.

Mutlu, M. et al., "Matrix Surface Modification by Plasma Polymerization for Enzyme Immobilization", Journal of Materials Chemistry, vol. 1, pp. 447-450, 1991.

Nakada, S. et al., "Hyperbranched Modification of Unsaturated Side Chains of Polyethylene Introduced by γ-Ray Irradiation Under a 1,3-Butadiene Atmosphere", Colloid & Polymer Science, vol. 279. pp. 754-762, 2001.

Oswald, P.R. at al., "Properties of Thermostable β-Glucosidase Immobilized Using Tris (Hydroxymethyl) Phosphine as a Highly Effective Coupling Agent", Enzyme and Microbial Technology, vol. 23, pp. 14-19, 1998.

Potezny, N. et al., "Urinary Oxalate Determination by Use of Immobilized Oxalate Oxidase in a Continuous-Flow System", Clinical Chemistry, vol. 29, pp. 16-20, Jan. 1983.

Pundir, C. et al., "Immobilization of Sorghum Leaf Oxalate Oxidase onto Alkylamine and Arylamine Glass", Chinese Journal of Biotechnology, vol. 15, pp. 129-138, 1999.

(56) References Cited

OTHER PUBLICATIONS

Reid, G. et al., "Microbial Adhesion and Biofilm Formation on Ureteral Stents in Vitro and in Vivo", Journal of Urology, vol. 148, pp. 1592-1594, Nov. 1992.
Robert, M. et al., "Double-J Ureteric Stent Encrustations: Clinical Study on Crystal Formation on Polyurethane Stents", Urologia Internationalis, vol. 58, pp. 100-104, 1997.
Santin, M. et al., "Effect of the Urine Conditioning Film on Ureteral Stent Encrustation and Characterization of its Protein Composition", Biomaterials, vol. 20, pp. 1245-1251, Jul. 1999.
Sidhu, H. et al., "Detection and Characterization of *Oxalobacter formigenes* Strains Using Oligonucleotide Probes", Meeting for Urolithaisis, pp. 537-539, 1996.
Solomons, C.C. et al., "Calcium Citrate for Vulvar Vestibulitis", The Journal of Reproductive Medicine, vol. 36, No. 12, pp. 879-882, 1991.
Thakur, M. et al., "Discrete Analysis of Plasma Oxalate with Alkylamine Glass Bound Sorghum Oxalate Oxidase and Horseradish Peroxidase", Journal of Biochemical and Biophysical Methods, vol. 44, pp. 77-88, Jul. 2000.
Tieszer, C. et al., "XPS and SEM Detection of Surface Changes on 64 Ureteral Stents after Human Usage", John Wiley & Sons, Inc., pp. 321-330, Dec. 1997.
Tieszer, C. et al., "Conditioning Film Deposition on Ureteral Stents After Implantation", Journal of Urology, vol. 160, pp. 876-881, Sep. 1998.
Tunney, M.M. et al., "Comparative Assessment of Ureteral Stent Biomaterial Encrustation", Biomaterials, vol. 17, pp. 1541-1546, Aug. 1996.
Urban, M.W. et al., "DMA and ATR FT-IR Studies of Gas Plasma Modified Silicone Elastomer Surfaces", Journal of Applied Polymer Science, vol. 39, pp. 265-283, 1990.
Wollin, T. et al., "Bacterial Biofilm Formation, Encrustation, and Antibiotic Adsorption to Ureteral Stents Indwelling in Humans", Journal of Endourology, vol. 12, pp. 101-111, 1998.
Xing, L.C. et al., "Oral Colon-Specific Drug Delivery for Bee Venom Peptide: Development of a Coated Calcium Alginate Gel Beads-Entrapped Lipsome", Journal of Controlled Release, vol. 93, pp. 293-300, Dec. 2003.
De Oliveria Neto, G. et al., "Oxalate Determination in Urine Using an Immobilized Enzyme on Sorghum Vulgare Seeds in a Flow Injection Conductimetric System", J. Braz. Chem. Soc., vol. 8, No. 1, pp. 47-51, 1997.
Barbalias, G. et al., "Encrustation of a Netal Alloy Urinary Stent: A Mechanistic Investigation", European Urology, Abstract, vol. 38, No. 2, pp. 1-2, 2000.
Sofer, M. et al., "Encrustation of Biomaterials in the Urinary Tract", Current Opinion in Urology, vol. 10, pp. 563-569, Nov. 2000.
International Search Report for PCT Application No. PCT/US2006/047909 dated Sep. 23, 2008.
International Search Report for PCT Application No. PCT/US2006/047967 dated Oct. 6, 2008.
Grases, Felix et al., "Study on Concretions Developed Around Urinary Catheters and Mechanisms of Renal Calculi Development", Nephron, vol. 88, pp. 320-328, Aug. 2000.
Sidhu, Harmeet et al., "Direct Quantification of the Enteric Bacterium *Oxalobacter formigenes* in Human Fecal Samples by Quantitative Competitive-Template PCR", Journal of Clinical Microbiology, vol. 37, No. 5, pp. 1503-1509, May 1999.
International Search Report for PCT Application No. PCT/US2005/045457 dated Jun. 4, 2008.
Lane, Byron G., "Oxalate, Germin, and the Extracellular Matrix of Higher Plants", The FASEB Journal, vol. 8, pp. 294-301, Mar. 1994.

Dominguez-Munoz, J.E. et al., "Effect of Oral Pancreatic Enzyme Administration on Digestive Function in Healthy Subjects: Comparison Between Two Enzyme Preparations", Aliment Pharmacol Ther., vol. 11, pp. 403-408, 1997.
Baetz, Albert L. et al., :Purification and Characterization of Oxalyl-Coenzyme A Decarboxylase from *Oxalobacter formigenes*, Journal of Bacteriology, vol. 171, No. 5, pp. 2605-2608, May 1989.
Baetz, Albert L. et al.; "Purification and Characterization of Formyl-Coenzyme A. Transferase from *Oxalobacter formigenes*", Journal of Bacteriology, vol. 172, No. 7, pp. 3537-3540, Jul. 1990.
International Search Report and Written Opinion for related PCT Application No. PCT/US2005/021134 dated Nov. 14, 2007.
Barreiro-Iglesias et al., "Preparation of chitosan beads by simultaneous cross-linking/insolubilisation in basic pH Rheological optimization and drug loading/release behaviour," European Journal of Pharmaceutical Sciences, vol. 24, pp. 77-84, 2005.
Remunan-Lopez et al., "Development of new chitosan-cellulose multicore microparticles for controlled drug delivery," European Journal of Pharmaceutics and Biopharmaceutics, vol. 45, pp. 49-56, 1998.
U.S. Appl. No. 13/919,266, filed Jun. 17, 2003, Allison et al.
U.S. Appl. No. 11/899,018, filed Aug. 31, 2007, Sidhu.
International Search Report issued on Nov. 15, 2010 in application No. PCT/EP2010/003864.
European Search Report issued on Sep. 4, 2009 in application No. EP 09 16 4430.
Khan et al., "A pH-Dependent Colon-Targeted Oral Drug Delivery System Using Methacrylic Acid Copolymers. II. Manipulation of Drug Release Using Eudragit® L100 and Eudragit S100 Combinations," Drug Development and Industrial Pharmacacy, vol. 26, No. 5, pp. 549-554, 2000.
Aoki et al., "Purification of Recombinant Human Pepsinogens and Their Application as Immunoassay Standards," Biochemistry and Molecular Biology International, vol. 45, No. 2, pp. 289-301, Jun. 1998.
Svedruzic et al., "The enzymes of oxalate metabolism: unexpected structures and mechanisms," Archives of Biochemistry and Biophysics, vol. 433, No. 1, pp. 176-192, 2005.
Svedruzic, Mechanism of the reaction catalyzed by the oxalate decarboxylase from *Bacillus subtilis*, A dissertation for Ph.D., pp. 1-102, University of Florida, 2005.
Campieri et al., "Reduction of olxuria after an oral course of lactic acid bacteria at high concentration," Kidney International, vol. 60, pp. 1097-1105, 2001.
European Search Report issued on Feb. 8, 2012 for application No. EP 06 84 8618 (corresponding to USP 8,545,836).
Kailasapathy, "Microencapsulation of probiotic bacteria: Technology and potential applications," Curr. Issues Intest. Microbiol., vol. 3, pp. 39-48, 2002.
Gombotz et al., "Protein release from alginate matrices," Advanced Drug Delivery Reviews, vol. 31, pp. 267-285, 1998.
Jin et al., "The Solution and Solid State Stability and Excipient Compatability of Parthenolide in Feverfew," AAPS Pharm Sci Tech, vol. 8, No. 4, pp. E1-E6, published on Dec. 14, 2007.
European Search Report issued on Feb. 9, 2009 in application No. EP 08168165 (corresponding to US 8,486,389).
Hoppe B, et al. (2005) Oxalate degrading bacteria: new treatment option for patients with primary and secondary hyperoxaluria, Urol Res. 33(5): 372-375.
Siva S, et al al. (2009) A critical analysis of the role of gut Oxalobacter formigenes in oxalate stone disease. BJU Int. 103(1): 18-21.
Khan M.Z.I., et al. (2000) A pH-dependent colon-targeted oral drug delivery system using methacrylic acid copolymers. II. Manipulation of drug release using Eudragit L 100 and Eudragit S 100 combinations. Drug Dev Ind Pharm. 26(5): 549-554.

\* cited by examiner

SEQUENCE LISTING

<160> NUMBER OF SEQ ID NOS: 10

<210> SEQ ID NO 1
<211> LENGTH: 568
<212> TYPE: PRT
<213> ORGANISM: Oxalobacter formigenes

<400> SEQUENCE: 1

Met Ser Asn Asp Asp Asn Val Glu Leu Thr Asp Gly Phe His Val Leu
1               5                   10                  15

Ile Asp Ala Leu Lys Met Asn Asp Ile Asp Thr Met Tyr Gly Val Val
            20                  25                  30

Gly Ile Pro Ile Thr Asn Leu Ala Arg Met Trp Gln Asp Gly Gln

```
                35                  40                  45
Arg Phe Tyr Ser Phe Arg His Glu Gln His Ala Gly Tyr Ala Ala Ser
 50                  55                  60

Ile Ala Gly Tyr Ile Glu Gly Lys Pro Gly Val Cys Leu Thr Val Ser
 65                  70                  75                  80

Ala Pro Gly Phe Leu Asn Gly Val Thr Ser Leu Ala His Ala Thr Thr
                 85                  90                  95

Asn Cys Phe Pro Met Ile Leu Leu Ser Gly Ser Ser Glu Arg Glu Ile
                100                 105                 110

Val Asp Leu Gln Gln Gly Asp Tyr Glu Glu Met Asp Gln Met Asn Val
            115                 120                 125

Ala Arg Pro His Cys Lys Ala Ser Phe Arg Ile Asn Ser Ile Lys Asp
        130                 135                 140

Ile Pro Ile Gly Ile Ala Arg Ala Val Arg Thr Ala Val Ser Gly Arg
145                 150                 155                 160

Pro Gly Gly Val Tyr Val Asp Leu Pro Ala Lys Leu Phe Gly Gln Thr
                165                 170                 175

Ile Ser Val Glu Glu Ala Asn Lys Leu Leu Phe Lys Pro Ile Asp Pro
            180                 185                 190

Ala Pro Ala Gln Ile Pro Ala Glu Asp Ala Ile Ala Arg Ala Ala Asp
        195                 200                 205

Leu Ile Lys Asn Ala Lys Arg Pro Val Ile Met Leu Gly Lys Gly Ala
210                 215                 220

Ala Tyr Ala Gln Cys Asp Asp Glu Ile Arg Ala Leu Val Glu Glu Thr
225                 230                 235                 240

Gly Ile Pro Phe Leu Pro Met Gly Met Ala Lys Gly Leu Leu Pro Asp
                245                 250                 255

Asn His Pro Gln Ser Ala Ala Thr Arg Ala Phe Ala Leu Ala Gln
            260                 265                 270

Cys Asp Val Cys Val Leu Ile Gly Ala Arg Leu Asn Trp Leu Met Gln
        275                 280                 285

His Gly Lys Gly Lys Thr Trp Gly Asp Glu Leu Lys Lys Tyr Val Gln
290                 295                 300

Ile Asp Ile Gln Ala Asn Glu Met Asp Ser Asn Gln Pro Ile Ala Ala
305                 310                 315                 320

Pro Val Val Gly Asp Ile Lys Ser Ala Val Ser Leu Leu Arg Lys Ala
                325                 330                 335

Leu Lys Gly Ala Pro Lys Ala Asp Ala Glu Trp Thr Gly Ala Leu Lys
            340                 345                 350

Ala Lys Val Asp Gly Asn Lys Ala Lys Leu Ala Gly Lys Met Thr Ala
        355                 360                 365

Glu Thr Pro Ser Gly Met Met Asn Tyr Ser Asn Ser Leu Gly Val Val
370                 375                 380

Arg Asp Phe Met Leu Ala Asn Pro Asp Ile Ser Leu Val Asn Glu Gly
385                 390                 395                 400

Ala Asn Ala Leu Asp Asn Thr Arg Met Ile Val Asp Met Leu Lys Pro
                405                 410                 415

Arg Lys Arg Leu Asp Ser Gly Thr Trp Gly Val Met Gly Ile Gly Met
            420                 425                 430

Gly Tyr Cys Val Ala Ala Ala Val Thr Gly Lys Pro Val Ile Ala
        435                 440                 445

Val Glu Gly Asp Ser Ala Phe Gly Phe Ser Gly Met Glu Leu Glu Thr
450                 455                 460
```

```
Ile Cys Arg Tyr Asn Leu Pro Val Thr Val Ile Met Asn Asn Gly
465                 470                 475                 480

Gly Ile Tyr Lys Gly Asn Glu Ala Asp Pro Gln Pro Gly Val Ile Ser
            485                 490                 495

Cys Thr Arg Leu Thr Arg Gly Arg Tyr Asp Met Met Met Glu Ala Phe
            500                 505                 510

Gly Gly Lys Gly Tyr Val Ala Asn Thr Pro Ala Glu Leu Lys Ala Ala
            515                 520                 525

Leu Glu Glu Ala Val Ala Ser Gly Lys Pro Cys Leu Ile Asn Ala Met
            530                 535                 540

Ile Asp Pro Asp Ala Gly Val Glu Ser Gly Arg Ile Lys Ser Leu Asn
545                 550                 555                 560

Val Val Ser Lys Val Gly Lys Lys
            565

<210> SEQ ID NO 2
<211> LENGTH: 2340
<212> TYPE: DNA
<213> ORGANISM: Oxalobacter formigenes

<400> SEQUENCE: 2
gagcaagatg agatgtcctt cctctgtggc aatcaggaat atattgacgg cacgtgtttt      60
ccctacttcc ggtgtgccag acatctccaa agatctcatg tggttttgga atccattttt     120
gccggtatcc cggctattcc ttacttttcc aaattgggtg taatgcaatg aatctatggt     180
ttttaatgct gtatggacaa ttttccggca gtgaaatttt cagatgcatt tcatttgtat     240
tcaggcggat ttgtttaaat tgacctgaat caatattgcc ggattgatct aggtcaatga     300
agtcaaattg acttatgtca atggtgccaa attgacctag gtcaacggga ttttttaaagg     360 gtatgcggca tactcggaat tgacgttaaa aacgtttat caaaaccaac caagaaaagg      420
tattactcat gagtaacgac acaatgtag agttgactga tggctttcat gttttgatcg     480
atgccctgaa aatgaatgac atcgatacca tgtatggtgt tgtcggcatt cctatcacga     540
acctggctcg tatgtggcaa gatgacggtc agcgttttta cagcttccgt cacgaacaac     600
acgcaggtta tgcagcttct atcgccggtt acatcgaagg aaaacctggc gtttgcttga     660
ccgtttccgc ccctggcttc ctgaacgcgc tgacttccct ggctcatgca accaccaact     720
gcttcccaat gatcctgttg agcggttcca gtgaacgtga atcgtcgat ttgcaacagg      780 gcgattacga agaaatggat cagatgaatg ttgcacgtcc acactgcaaa gcttctttcc     840
gtatcaacag catcaaagac attccaatcg gtatcgctcg tgcagttcgc accgctgtat     900
ccggacgtcc aggtggtgtt tacgttgact tgccagcaaa actgttcggt cagaccattt     960
ctgtagaaga agctaacaaa ctgctcttca aaccaatcga tccagctccg gcacagattc    1020
ctgctgaaga cgctatcgct cgcgctgctg acctgatcaa gaacgccaaa cgtccagtta    1080
tcatgctggg taaaggcgct gcatacgcac aatgcgacga cgaaatccgc gcactggttg    1140
aagaaaccgg catcccattc ctgccaatgg gtatggctaa aggcctgctg cctgacaacc    1200
atccacaatc cgctgctgca cccgtgctt tcgcactggc acagtgtgac gtttgcgtac     1260
tgatcggcgc tcgtctgaac tggctgatgc agcacggtaa aggcaaaacc tggggcgacg    1320
aactgaagaa atacgttcag atcgacatcc aggctaacga aatggacagc aaccagccta    1380
tcgctgcacc agttgttggt gacatcaagt ccgccgtttc cctgctccgc aaagcactga    1440
aaggcgctcc aaaagctgac gctgaatgga ccggcgctct gaaagccaaa gttgacggca    1500
```

```
acaaagccaa actggctggc aagatgactg ccgaaacccc atccggaatg atgaactact    1560
ccaattccct gggcgttgtt cgtgacttca tgctggcaaa tccggatatt tccctggtta    1620
acgaaggcgc taatgcactc gacaacactc gtatgattgt tgacatgctg aaaccacgca    1680
aacgtcttga ctccggtacc tggggtgtta tgggtattgg tatgggctac tgcgttgctg    1740
cagctgctgt taccggcaaa ccggttatcg ctgttgaagg cgatagcgca ttcggtttct    1800
ccggtatgga actggaaacc atctgccgtt acaacctgcc agttaccgtt atcatcatga    1860
acaatggtgg tatctataaa ggtaacgaag cagatccaca accaggcgtt atctcctgta    1920
cccgtctgac ccgtggtcgt tacgacatga tgatggaagc atttggcggt aaaggttatg    1980
ttgccaatac tccagcagaa ctgaaagctg ctctggaaga agctgttgct tccggcaaac    2040
catgcctgat caacgcgatg atcgatccag acgctggtgt cgaatctggc cgtatcaaga    2100
gcctgaacgt tgtaagtaaa gttggcaaga ataattagc ccaactttga tgaccggtta    2160
cgaccggtca cataaagtgt tcgaatgccc ttcaagttta cttgaagggc attttttac    2220 cttgcagttt ataaacagga aaaattgaag tattcagagc ggaaaagcag atttaagcca    2280
cgagaaacat tcttttttat tgaaaattgc cataaacaca ttttaaagc tggctttttt    2340
```

<210> SEQ ID NO 3
<211> LENGTH: 428
<212> TYPE: PRT
<213> ORGANISM: Oxalobacter formigenes

<400> SEQUENCE: 3

```
Met Thr Lys Pro Leu Asp Gly Ile Asn Val Leu Asp Phe Thr His Val
1               5                   10                  15

Gln Ala Gly Pro Ala Cys Thr Gln Met Met Gly Phe Leu Gly Ala Asn
            20                  25                  30

Val Ile Lys Ile Glu Arg Arg Gly Ser Gly Asp Met Thr Arg Gly Trp
        35                  40                  45

Leu Gln Asp Lys Pro Asn Val Asp Ser Leu Tyr Phe Thr Met Phe Asn
    50                  55                  60

Cys Asn Lys Arg Ser Ile Glu Leu Asp Met Lys Thr Pro Glu Gly Lys
65                  70                  75                  80

Glu Leu Leu Glu Gln Met Ile Lys Lys Ala Asp Val Met Val Glu Asn
                85                  90                  95

Phe Gly Pro Gly Ala Leu Asp Arg Met Gly Phe Thr Trp Glu Tyr Ile
            100                 105                 110

Gln Glu Leu Asn Pro Arg Val Ile Leu Ala Ser Val Lys Gly Tyr Ala
        115                 120                 125

Glu Gly His Ala Asn Glu His Leu Lys Val Tyr Glu Asn Val Ala Gln
    130                 135                 140

Cys Ser Gly Gly Ala Ala Ala Thr Thr Gly Phe Trp Asp Gly Pro Pro
145                 150                 155                 160

Thr Val Ser Gly Ala Ala Leu Gly Asp Ser Asn Ser Gly Met His Leu
                165                 170                 175

Met Ile Gly Ile Leu Ala Ala Leu Glu Met Arg His Lys Thr Gly Arg
            180                 185                 190

Gly Gln Lys Val Ala Val Ala Met Gln Asp Ala Val Leu Asn Leu Val
        195                 200                 205

Arg Ile Lys Leu Arg Asp Gln Gln Arg Leu Glu Arg Thr Gly Ile Leu
    210                 215                 220
```

```
Ala Glu Tyr Pro Gln Ala Gln Pro Asn Phe Ala Phe Asp Arg Asp Gly
225                 230                 235                 240

Asn Pro Leu Ser Phe Asp Asn Ile Thr Ser Val Pro Arg Gly Gly Asn
            245                 250                 255

Ala Gly Gly Gly Gln Pro Gly Trp Met Leu Lys Cys Lys Gly Trp
        260                 265                 270

Glu Thr Asp Ala Asp Ser Tyr Val Tyr Phe Thr Ile Ala Ala Asn Met
        275                 280                 285

Trp Pro Gln Ile Cys Asp Met Ile Asp Lys Pro Glu Trp Lys Asp Asp
    290                 295                 300

Pro Ala Tyr Asn Thr Phe Glu Gly Arg Val Asp Lys Leu Met Asp Ile
305                 310                 315                 320

Phe Ser Phe Ile Glu Thr Lys Phe Ala Asp Lys Asp Lys Phe Glu Val
                325                 330                 335

Thr Glu Trp Ala Ala Gln Tyr Gly Ile Pro Cys Gly Pro Val Met Ser
            340                 345                 350

Met Lys Glu Leu Ala His Asp Pro Ser Leu Gln Lys Val Gly Thr Val
        355                 360                 365

Val Glu Val Val Asp Glu Ile Arg Gly Asn His Leu Thr Val Gly Ala
370                 375                 380

Pro Phe Lys Phe Ser Gly Phe Gln Pro Glu Ile Thr Arg Ala Pro Leu
385                 390                 395                 400

Leu Gly Glu His Thr Asp Glu Val Leu Lys Glu Leu Gly Leu Asp Asp
            405                 410                 415

Ala Lys Ile Lys Glu Leu His Ala Lys Gln Val Val
        420                 425

<210> SEQ ID NO 4
<211> LENGTH: 1579
<212> TYPE: DNA
<213> ORGANISM: Oxalobacter formigenes

<400> SEQUENCE: 4
aagcttgctt cattttgaga tgttatgcga agtgttagca acccaagtta gtaccttcag      60
cccctttggc gaagtttttc tttcttggca gttcctttcg gggaaacagc cacagagaat     120
aaaaaccaaa agttgtacca acgacaagga aatgagaaat tatgactaaa ccattagatg     180
gaattaatgt gcttgacttt acccacgtcc aggcaggtcc tgcctgtaca cagatgatgg     240
gtttcttggg cgcaaacgtc atcaagattg aaagacgtgg ttccggagat atgactcgtg     300
gatggctgca ggacaaacca aatgttgatt ccctgtattt cacgatgttc aactgtaaca     360
aacgttcgat tgaactggac atgaaaaccc cggaaggcaa agagcttctg aacagatga     420 tcaagaaagc cgacgtcatg gtcgaaaact tcggaccagg cgcactggac cgtatgggct     480
ttacttggga atacattcag gaactgaatc cacgcgtcat tctggcttcc gttaaaggct     540
atgcagaagg ccacgccaac gaacacctga agtttatga aaacgttgca cagtgttccg     600
gcggtgctgc agctaccacc ggtttctggg atggtcctcc aaccgtttcc ggcgctgctc     660
tgggtgactc caactccggt atgcacctga tgatcggtat tctggccgct ctggaaatgc     720
gtcacaaaac cggccgtggt cagaaagttg ccgtcgctat gcaggacgct gttctgaatc     780
tggttcgtat caaactgcgt gaccagcaac gtctggaaag aaccggcatt ctggctgaat     840
acccacaggc tcagcctaac tttgccttcg acagagacgg taaccactg tccttcgaca     900 acatcacttc cgttccacgt ggtggtaacg caggtggcgg cggccagcca ggctggatgc     960
```

```
tgaaatgtaa aggttgggaa accgatgcgg actcctacgt ttacttcacc atcgctgcaa    1020
acatgtggcc acagatctgc gacatgatcg acaagccaga atggaaagac gacccagcct    1080
acaacacatt cgaaggtcgt gttgacaagc tgatggacat cttctccttc atcgaaacca    1140
agttcgctga caaggacaaa ttcgaagtta ccgaatgggc tgcccagtac ggcattcctt    1200
gcggtccggt catgtccatg aaagaactgg ctcacgatcc ttccctgcag aaagttggta    1260
ccgtcgttga agttgtcgac gaaattcgtg gtaaccacct gaccgttggc gcaccgttca    1320
aattctccgg attccagccg gaaattaccc gtgctccgct gttgggcgaa cataccgacg    1380
aagttctgaa agaactgggt cttgacgatg ccaagatcaa ggaactgcat gcaaaacagg    1440
tagtttgatc cgtcagactt tctgggcaaa acggcactct ccggagtgcc gttttttgt     1500 cacacgaaac cctaatcaaa caagcacgtg caatgattcc acatcattgc ggccacattc    1560
atccttcggg tcattactg                                                  1579
```

<210> SEQ ID NO 5
<211> LENGTH: 385
<212> TYPE: PRT
<213> ORGANISM: Bacillus subtilis

<400> SEQUENCE: 5

```
Met Lys Lys Gln Asn Asp Ile Pro Gln Pro Ile Arg Gly Asp Lys Gly
1               5                   10                  15

Ala Thr Val Lys Ile Pro Arg Asn Ile Glu Arg Asp Arg Gln Asn Pro
            20                  25                  30

Asp Met Leu Val Pro Pro Glu Thr Asp His Gly Thr Val Ser Asn Met
        35                  40                  45

Lys Phe Ser Phe Ser Asp Thr His Asn Arg Leu Glu Lys Gly Gly Tyr
    50                  55                  60

Ala Arg Glu Val Thr Val Arg Glu Leu Pro Ile Ser Glu Asn Leu Ala
65                  70                  75                  80

Ser Val Asn Met Arg Leu Lys Pro Gly Ala Ile Arg Glu Leu His Trp
                85                  90                  95

His Lys Glu Ala Glu Trp Ala Tyr Met Ile Tyr Gly Ser Ala Arg Val
            100                 105                 110

Thr Ile Val Asp Glu Lys Gly Arg Ser Phe Ile Asp Asp Val Gly Glu
        115                 120                 125

Gly Asp Leu Trp Tyr Phe Pro Ser Gly Leu Pro His Ser Ile Gln Ala
    130                 135                 140

Leu Glu Glu Gly Ala Glu Phe Leu Leu Val Phe Asp Asp Gly Ser Phe
145                 150                 155                 160

Ser Glu Asn Ser Thr Phe Gln Leu Thr Asp Trp Leu Ala His Thr Pro
                165                 170                 175

Lys Glu Val Ile Ala Ala Asn Phe Gly Val Thr Lys Glu Glu Ile Ser
            180                 185                 190

Asn Leu Pro Gly Lys Glu Lys Tyr Ile Phe Glu Asn Gln Leu Pro Gly
        195                 200                 205

Ser Leu Lys Asp Asp Ile Val Glu Gly Pro Asn Gly Glu Val Pro Tyr
    210                 215                 220

Pro Phe Thr Tyr Arg Leu Leu Glu Gln Glu Pro Ile Glu Ser Glu Gly
225                 230                 235                 240

Gly Lys Val Tyr Ile Ala Asp Ser Thr Asn Phe Lys Val Ser Lys Thr
                245                 250                 255

Ile Ala Ser Ala Leu Val Thr Val Glu Pro Gly Ala Met Arg Glu Leu
```

```
                    260                 265                 270
His Trp His Pro Asn Thr His Glu Trp Gln Tyr Tyr Ile Ser Gly Lys
                275                 280                 285

Ala Arg Met Thr Val Phe Ala Ser Asp Gly His Ala Arg Thr Phe Asn
            290                 295                 300

Tyr Gln Ala Gly Asp Val Gly Tyr Val Pro Phe Ala Met Gly His Tyr
305                 310                 315                 320

Val Glu Asn Ile Gly Asp Glu Pro Leu Val Phe Leu Glu Ile Phe Lys
                325                 330                 335

Asp Asp His Tyr Ala Asp Val Ser Leu Asn Gln Trp Leu Ala Met Leu
            340                 345                 350

Pro Glu Thr Phe Val Gln Ala His Leu Asp Leu Gly Lys Asp Phe Thr
                355                 360                 365

Asp Val Leu Ser Lys Glu Lys His Pro Val Val Lys Lys Cys Ser
            370                 375                 380

Lys
385

<210> SEQ ID NO 6
<211> LENGTH: 1158
<212> TYPE: DNA
<213> ORGANISM: Bacillus subtilis

<400> SEQUENCE: 6
atgaaaaaac aaaatgacat tccgcagcca attagaggag acaaaggagc aacggtaaaa      60
atcccgcgca atattgaaag agaccggcaa aaccctgata tgctcgttcc gcctgaaacc     120
gatcatggca ccgtcagcaa tatgaagttt tcattctctg atactcataa ccgattagaa     180
aaaggcggat atgcccggga agtgacagta cgtgaattgc cgatttcaga aaaccttgca     240
tccgtaaata tgcggctgaa gccaggcgcg attcgcgagc ttcactggca taagaagct      300 gaatgggctt atatgattta cggaagtgca agagtcacaa ttgtagatga aaagggcgc      360 agctttattg acgatgtagg tgaaggagac ctttggtact tcccgtcagg cctgccgcac     420
tccatccaag cgctggagga gggagctgag ttcctgctcg tgtttgacga tggatcattc     480
tctgaaaaca gcacgttcca gctgacagat tggctggccc acactccaaa agaagtcatt     540
gctgcgaact cggcgtgac aaaagaagag atttccaatt tgcctggcaa agaaaaatat     600
atatttgaaa accaacttcc tggcagttta aaagatgata ttgtggaagg gccgaatggc     660
gaagtgcctt atccatttac ttaccgcctt cttgaacaag agccgatcga atctgaggga     720
ggaaaagtat acattgcaga ttcgacaaac ttcaaagtgt ctaaaaccat cgcatcagcg     780
ctcgtaacag tagaacccgg cgccatgaga gaactgcact ggcacccgaa tacccacgaa     840
tggcaatact acatctccgg taaagctaga tgaccgtttt ttgcatctga cggccatgcc     900
agaacgttta attaccaagc cggtgatgtc ggatatgtac catttgcaat gggtcattac     960
gttgaaaaca tcggggatga accgcttgtc tttttagaaa tcttcaaaga cgaccattat    1020
gctgatgtat cttttaaacca atggcttgcc atgcttcctg aaacatttgt tcaagcgcac    1080
cttgacttgg gcaaagactt tactgatgtg ctttcaaaag aaaagcaccc agtagtgaaa    1140
aagaaatgca gtaaataa                                                  1158

<210> SEQ ID NO 7
<211> LENGTH: 224
<212> TYPE: PRT
<213> ORGANISM: Hordeum vulgare
```

<400> SEQUENCE: 7

```
Met Gly Tyr Ser Lys Asn Leu Gly Ala Gly Leu Phe Thr Met Leu Leu
1               5                   10                  15
Leu Ala Pro Ala Ile Met Ala Thr Asp Pro Asp Pro Leu Gln Asp Phe
            20                  25                  30
Cys Val Ala Asp Leu Asp Gly Lys Ala Val Ser Val Asn Gly His Thr
        35                  40                  45
Cys Lys Pro Met Ser Glu Ala Gly Asp Asp Phe Leu Phe Ser Ser Lys
    50                  55                  60
Leu Thr Lys Ala Gly Asn Thr Ser Thr Pro Asn Gly Ser Ala Val Thr
65                  70                  75                  80
Glu Leu Asp Val Ala Glu Trp Pro Gly Thr Asn Thr Leu Gly Val Ser
                85                  90                  95
Met Asn Arg Val Asp Phe Ala Pro Gly Gly Thr Asn Pro Pro His Ile
            100                 105                 110
His Pro Arg Ala Thr Glu Ile Gly Met Val Met Lys Gly Glu Leu Leu
        115                 120                 125
Val Gly Ile Leu Gly Ser Phe Asp Ser Gly Asn Lys Leu Tyr Ser Arg
    130                 135                 140
Val Val Arg Ala Gly Glu Thr Phe Val Ile Pro Arg Gly Leu Met His
145                 150                 155                 160
Phe Gln Phe Asn Val Gly Lys Thr Glu Ala Tyr Met Val Val Ser Phe
                165                 170                 175
Asn Ser Gln Asn Pro Gly Ile Val Phe Val Pro Leu Thr Leu Phe Gly
            180                 185                 190
Ser Asn Pro Pro Ile Pro Thr Pro Val Leu Thr Lys Ala Leu Arg Val
        195                 200                 205
Glu Ala Gly Val Val Glu Leu Leu Lys Ser Lys Phe Ala Gly Gly Ser
    210                 215                 220
```

<210> SEQ ID NO 8
<211> LENGTH: 970
<212> TYPE: DNA
<213> ORGANISM: Hordeum vulgare

<400> SEQUENCE: 8

```
agcttagcag caaccaccag tagtgcctca aaggctcctg atcaacaaac tctagctcat      60
cagtggtagc taagcttgct acatagcaag caatgggtta ctctaaaaac ctaggggctg     120
gcctgttcac catgctgctc cttgctccgg ccatcatggc taccgaccct gaccctctac     180
aggacttctg cgtcgcggac ctcgatggca aggcggtctc ggtgaacggg catacgtgta     240
agcccatgtc ggaggccggc gacgacttcc tcttctcgtc caagctgacc aaggccggca     300
acacgtccac cccgaacggc tcggccgtga cggagctcga cgtggccgag tggcccggta     360
cgaacacgct gggcgtgtcc atgaaccgtg tggacttcgc cgggcggc accaaccccg     420
cgcacatcca cccgcgtgca accgagatcg gcatggtgat gaaggtgag ctcctcgttg     480
gaatcctcgg cagctttgac tccggaaaca agctctactc cagggtggtg cgtgccggag     540
agactttcgt catcccgcgc ggcctcatgc acttccagtt caacgttggt aagacggaag     600
cctacatggt tgtgtccttc aacagccaga accctggcat cgtcttcgtg ccgctcacac     660
tcttcggttc caacccgccc atccccacac cggtgctcac caaggctctt cgggtggagg     720
ccggggtcgt ggaacttctc aagtccaagt tcgccggtgg gtcttaactt ccatgagccc     780
```

```
caaatgatca atatgaatat gtaattctat atatccatgt atgctgcgaa tttaatagta    840
ctcgacagga gactatattc aagcttctgg ataagctcgc atttcatagt aataagattg    900
aataagttat cctagcggtt cagccttcag aaccaatgcg aggacttaaa atgtattgct    960
tcttattatt                                                          970
```

<210> SEQ ID NO 9
<211> LENGTH: 1152
<212> TYPE: DNA
<213> ORGANISM: Bacillus subtilis

<400> SEQUENCE: 9

```
aaaaaacaaa atgacattcc gcagccaatt agaggagaca aaggagcaac ggtaaaaatc     60
ccgcgcaata ttgaaagaga ccggcaaaac cctgatatgc tcgttccgcc tgaaaccgat    120
catggcaccg tcagcaatat gaagttttca ttctctgata ctcataaccg attagaaaaa    180
ggcggatatg cccgggaagt gacagtacgt gaattgccga tttcagaaaa ccttgcatcc    240
gtaaatatgc ggctgaagcc aggcgcgatt cgcgagcttc actggcataa agaagctgaa    300 tgggctttata tgatttacgg aagtgcaaga gtcacaattg tagatgaaaa agggcgcagc    360
tttattgacg atgtaggtga aggagccctt tggtacttcc cgtcaggcct gccgcactcc    420
atccaagcgc tggaggaggg agctgagttc ctgctcgtgt ttgacgatgg atcattctct    480
gaaaacagca cgttccagct gacagattgg ctggcccaca ctccaaaaga agtcattgct    540
gcgaacttcg gcgtgacaaa agaagagatt ccaatttgc ctggcaaaga aaatatata      600 tttgaaaacc aacttcctgg cagttttaaa gatgatattg tggaagggcc gaatggcgaa    660
gtgccttatc catttactta ccgccttctt gaacaagagc cgatcgaatc tgagggagga    720
aaagtataca ttgcagattc gacaaacttc aaagtgtcta aaaccatcgc atcagcgctc    780
gtaacagtag aacccggcgc catgagagaa ctgcactggc acccgaatac ccacgaatgg    840
caatactaca tctccggtaa agctagaatg accgttttg catctgacgg ccatgccaga     900
acgtttaatt accaagccgg tgatgtcgga tatgtaccat ttgcaatggg tcattacgtt    960
gaaaacatcg gggatgaacc gcttgtcttt ttagaaatct tcaaagacga ccattatgct   1020
gatgtatctt taaccaatg gcttgccatg cttcctgaaa catttgttca agcgcacctt   1080
gacttgggca agactttac tgatgtgctt tcaaaagaaa agcacccagt agtgaaaaag   1140
aaatgcagta aa                                                      1152
```

<210> SEQ ID NO 10
<211> LENGTH: 1164
<212> TYPE: DNA
<213> ORGANISM: Artificial sequence
<220> FEATURE:
<223> OTHER INFORMATION: Yvrk gene sequence optimized for E. coli with
      restriction sites at the 5' and 3' ends

<400> SEQUENCE: 10

```
catatgaaaa acagaatga cattccacag ccgattcgcg gcgataaagg cgcgaccgtc     60
aaaattcctc gcaatatcga acgcgaccgc cagaatccgg atatgctggt gccgccggag    120
acggaccatg gcacggtgtc taacatgaaa ttctcttta gcgataccca caaccgcctg    180 gaaaaggtg gctacgcgcg cgaggttacc gtccgtgaac tgccaattag cgaaaatctg    240
gcttcggtta acatgcgtct gaaaccaggt gctatccgtg agctgcactg gcacaaggaa    300
gcggaatggg cgtatatgat ttacggttca gcacgtgtta ccatcgtaga cgagaaaggt    360
```

-continued

```
cgtagcttta tcgatgatgt tggcgaaggt gatctgtggt atttcccatc tggcctgccg      420
cattcgattc aggcgctgga agaaggcgct gaatttctgc tggtgttcga tgatggttcc      480
ttttctgaaa acagcacgtt ccagctgacg gattggctgg cgcacacgcc gaaagaagtc      540
attgcggcca attttggggt aaccaaagaa gaaatttcca acctgccggg caaagaaaag      600 tatattttg  agaatcagct gccgggctct ctgaaggacg atattgtaga aggccctaac      660
ggtgaggtgc cgtatccgtt cacctatcgt ctgctggagc aggaaccgat tgaaagcgaa      720
ggcggtaaag tttatatcgc agattccact aactttaaag tctccaagac cattgccagc      780
gccctggtca ccgtggaacc gggagcgatg cgcgagctgc actggcatcc gaacacgcac      840
gaatggcagt attatatttc cggcaaagca cgcatgaccg tttttgcctc agatggacac      900
gctcgcacgt ttaattatca agcgggtgat gttggctacg ttcctttcgc catgggccat      960
tatgtagaaa atatcggcga tgaaccactg gtgtttctgg agatctttaa agatgaccac     1020
tatgccgatg tttcactgaa tcagtggctg gccatgctgc cggaaacttt tgttcaggcg     1080
catctggacc tgggtaaaga ctttacggat gtgctgagca aagaaaaaca cccggtagtc     1140
aagaagaaat gcagtaaagg atcc                                             1164
```

COMPOSITIONS AND METHODS FOR OXALATE REDUCTION

RELATED APPLICATIONS

This application claims the priority of U.S. Provisional Patent Application No. 60/750,896, filed Dec. 16, 2005, which is herein incorporated in its entirety.

FIELD OF THE INVENTION

The present invention relates to a composition comprising one or more oxalate degrading enzymes for delivering the enzymes in active form to the stomach, where the one or more oxalate degrading enzymes exert their effect. Thus, the present invention provides means for reducing oxalate in the stomach. A composition of the invention comprises particles comprising one or more oxalate degrading enzymes embedded in a first polymeric material, wherein the embedded enzyme retains at least two times the activity of the one or more non-embedded free enzymes obtained from the same batch upon incubation in USP simulated gastric juice at 37° C. for at least 60 min under similar conditions.

BACKGROUND OF THE INVENTION

Kidney/urinary tract stone disease (urolithiasis) is a major health problem throughout the world. Most of the stones associated with urolithiasis are composed of calcium oxalate alone or calcium oxalate plus calcium phosphate. Other disease states have also been associated with excess oxalate. These include, vulvodynia, oxalosis associated with end-stage renal disease, cardiac conductance disorders, Crohns's disease, and other enteric disease states.

Oxalic acid, and/or its salts, oxalate, is found in a wide variety of foods, and is therefore, a component of many constituents in human and animal diets. Increased oxalate absorption may occur after foods containing elevated amounts of oxalic acid are eaten. Foods such as spinach and rhubarb are well known to contain high amounts of oxalate, but a multitude of other foods and beverages also contain oxalate. Because oxalate is found in such a wide variety of foods, diets that are low in oxalate and which are also palatable are hard to formulate. In addition, compliance with a low oxalate diet is often problematic.

The risk for formation of kidney stones revolves around a number of factors that are not yet completely understood. Kidney or urinary tract stone disease occurs in as many as 12% of the population in Western countries and about 70% of these stones are composed of calcium oxalate or of calcium oxalate plus calcium phosphate. Some individuals (e.g. patients with intestinal disease such as Crohn's disease, inflammatory bowel disease, or steatorrhea and also patients that have undergone jejunoileal bypass surgery) absorb more of the oxalate in their diets than do others. For these individuals, the incidence of oxalate urolithiasis increases markedly. The increased disease incidence is due to increased levels of oxalate in kidneys and urine, and this, the most common hyperoxaluric syndrome in humans, is known as enteric hyperoxaluria. Oxalate is also a problem in patients with end-stage renal disease and there is recent evidence that elevated urinary oxalate is also involved in vulvar vestibulitis (vulvodynia).

Enteric coated compositions comprising oxalate degrading bacteria have been suggested for reducing oxalate concentrations. However, enteric coated compositions pass through the stomach in intact form, i.e. the coating is intact and accordingly, no oxalate can be degraded in the stomach. Accordingly, there is still a need for developing compositions that enable degradation of oxalate already in the stomach in order to degrade especially dietary oxalate. Moreover, such compositions are suitable for use in the treatment of enteric and absorptive hyperoxalurias such as hyperoxalurias causing recurrent stone disease. The objective with such a treatment is for the patients to have normal urinary oxalate levels.

SUMMARY OF THE INVENTION

The present invention comprises compositions and methods for treating and preventing oxalate-related conditions. Compositions of the present invention comprise enzymes that reduce oxalate. Methods of the present invention comprise administering the compositions to treat or prevent oxalate-related conditions, and methods for making and using such compositions. Compositions of the present invention reduce oxalate under gastric conditions, such as low pH and in the presence of proteases. Composition of the present invention reduce oxalate in the stomach of humans and other animals. Compositions reduce non-systemic oxalate, e.g. oxalate in the gastrointestinal tract, notably in the stomach, and preventing exogenous oxalate (e.g. from food) from entering the systemic circulation.

A composition according to the present invention comprises particles comprising one or more enzymes embedded in a first polymeric material, wherein the embedded enzymes retain at least two times the activity of the one or more non-embedded enzymes from the same batch, after incubation of both the embedded and the non-embedded (free) enzymes in simulated gastric fluid (84 mM HCl and 3.2 mg/ml pepsin at pH ranging from 1.0 to 4.0) at 37° C. for at least 60 minutes. Compositions comprise particles that may further be coated with a second polymeric material.

Compositions may also comprise polymeric materials that may be cross-linked, and optionally, the cross-links may be reduced. In specific embodiments, the first polymeric material is chitosan, alginate, pectin or hyaluronic acid. In addition to the one or more enzymes and the first polymeric material, the particle compositions may also contain one or more additives such as, e.g., pH adjusting agents, buffering agents, solubilizing agents, stabilizers, preservatives, cofactors for the enzymes or one or more pharmaceutically acceptable excipients such as, e.g. fillers, diluents, carriers or the like.

Methods of the present invention comprise providing compositions for non-systemic treatment, for example, providing a composition that enables reducing oxalate in the stomach to avoid the absorption of oxalate from the gastrointestinal tract. The composition protects the oxalate-reducing enzymes embedded therein from the acidic and enzyme-damaging environment in the stomach, and maintains the enzymatic activity in such a harsh environment. Methods of treatment and prevention comprise providing the compositions taught herein in which one or more oxalate degrading enzyme are embedded in a first polymeric material, optionally coating the obtained particles with a second polymeric material, optionally cross-linking the first and/or second polymeric material and optionally reducing the cross-linkages.

The compositions of the present invention are suitable in methods of treatment or prevention of oxalate-related conditions including, but not limited to, hyperoxaluria, absorptive hyperoxaluria, enteric hyperoxaluria, primary hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and patients who have undergone gastrointestinal surgery and bariatric surgery (surgery for obesity), and/or who have undergone antibiotic treatment. A method of treatment or prevention comprises orally administering to a subject a composition of the present invention, in an effective amount, to reduce the oxalate in the stomach of the subject, and thus reduce the overall oxalate burden of the subject in an efficient and effective manner. Such compositions are pharmaceutically acceptable for oral administration.

Enzymes used in the compositions and methods of the present invention are oxalate reducing enzymes, and include, but are not limited to, oxalate oxidase, oxalate decarboxylase (in the present context abbreviated OxDc), oxalyl-CoA decarboxylase, or formyl-CoA transferase, or combinations thereof. Moreover, other enzymes, cofactors and co-enzymes that are substituents of oxalate degradation pathways or involved in oxalate metabolic pathways, particularly oxalate reduction, are also of relevance alone or in combination with one or more of the oxalate reducing enzymes. In the present invention, not only the enzymes (proteins) are encompassed by this definition, but also polynucleotide sequences that encode oxalate-reducing genes and proteins are contemplated by the present invention. The present invention also contemplates any binding partners of these enzymes and includes antibodies and antibody fragments that bind to or interact with the enzymes.

The enzymes may be derived by isolation from organisms, they may be purified, they may be made synthetically, semi-synthetically or by recombinant means, or they may be used as a cell lysate. The enzymes used in the compositions may be purified recombinant protein, but since the enzymes can also be made in certain bacteria that are safe, it is also contemplated to use those bacteria as whole cells or as lysate.

The oxalate-degrading enzyme is normally present in a composition of the invention in an amount that is sufficient to degrade substantially all oxalate normally present in a standard meal. Depending on the food choices, an average Western diet can contain 100 to 300 mg of oxalate/day. In general, about 0.2 g of the particles comprising enzyme (equal to 20 mg of OxDc in 1 mL of suspension of particles) can remove 180 mg oxalate in simulated gastric conditions within 30 min.

One aspect the present invention comprises a composition comprising particles comprising one or more oxalate degrading enzymes embedded in a first polymeric material, wherein the embedded enzyme retains at least two times the activity of the one or more non-embedded free enzymes, obtained from the same batch, upon incubation in USP simulated gastric juice containing 84 mM HCl and 3.2 mg/ml pepsin at pH>1, e.g. in a range of pH about 1 to pH about 5, such as, e.g., from pH about 2 to pH about 5, from pH about 2.5 to pH about 4.5, from pH about 2.5 to pH about 3.5 such as pH about 3 at 37° C. for at least 60 minutes.

DESCRIPTION OF THE FIGURES

FIG. 3. The volume statistics (Arithmetic) 17795s3__07__01.$1s. Calculations from 0.040 μm to 2000 μm. Volume: 100%; Mean: 48.53 μm; Median: 29.10 μm; Mean/Median ratio: 1.668; Mode: 28.70 μm; S.D.: 65.43 μm; C.V. 135%; Skewness: 4.384 Right skewed; Kurtosis 26.90 Leptokurtic; $d_{10}$ 8.814 μm; $d_{50}$ 29.10 μm; $d_{90}$ 109.9 μm.

DETAILED DESCRIPTION

Figure 1:
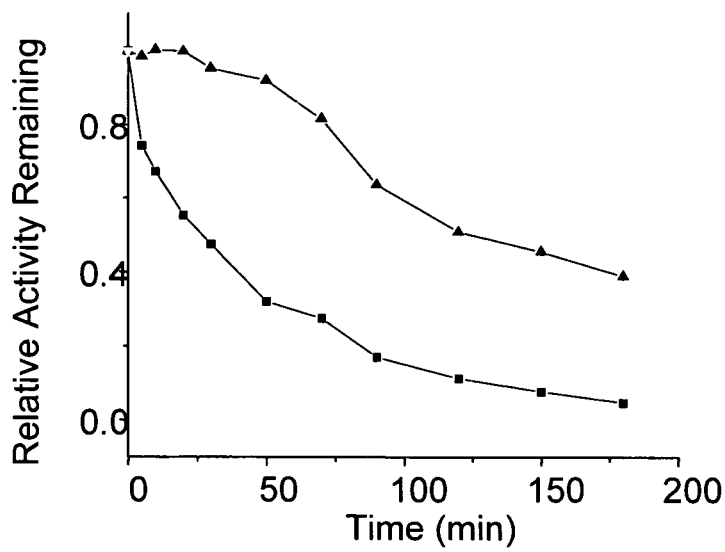
FIG. 1 is a graph showing the stability of OxDc in microparticles I (prepared at pH 3.9) and in microparticles II (prepared at pH 8) under pH 3 with pepsin.

The present invention comprises compositions and methods for treating and preventing oxalate-related conditions. Compositions of the present invention comprise enzymes that reduce oxalate. The compositions of the present invention are designed so that the enzymes retain their activity even if the compositions are subjected to a gastric environment. Methods of the present invention comprise administering the compositions to treat or prevent oxalate-related conditions, and methods for making and using such compositions. More specific, the invention relates to a composition that is designed to enable reduction of oxalate under gastric conditions, thereby enabling a reduction of oxalate already in the stomach. Such a composition is specifically designed to reduce non-systemic oxalate, e.g. oxalate in the gastrointestinal tract, notably in the stomach, and preventing exogenous oxalate (e.g. from food) from entering the systemic circulation.

As mentioned above, the background of the present invention was the need to be able to administer oxalate degrading enzymes to the stomach in order to degrade dietary oxalate and prevent the uptake of oxalate from the stomach and intestinal tract, which prevents oxalate-related diseases and disorders, such as, e.g., hyperoxaluria, primary hyperoxaluria, idiopathic calcium oxalate kidney stone disease (urothiliasis), and especially the absorptive and enteric hyperoxaluria. The administered enzymes are protected from the protein degradation and/or pH or acidic dependent degradation occurring under gastric conditions of the stomach, i.e. low pH and in the presence of pepsin.

Thus, the present invention relates to a composition, wherein the enzymes are embedded in a polymeric material which protects the enzymes from degradation under gastric conditions. It can be envisaged that this composition may comprise any enzyme, but for the purpose of the present invention, oxalate degrading enzymes, such as, e.g., oxalate decarboxylase, oxalate oxidase, or a combination of oxalyl-CoA decarboxylase and formyl CoA transferase, or a combination of any of these, is contemplated by the present invention.

A composition according to the present invention comprises particles comprising one or more enzymes embedded in a first polymeric material, wherein the embedded enzymes retain at least two times the activity of the one or more non-embedded enzymes from the same batch, after incubation of both the embedded and the non-embedded (free) enzymes in simulated gastric fluid (84 mM HCl and 3.2 mg/ml pepsin at pH ranging from 1.0 to 4.0) at 37° C. for at least 60 minutes. The particles may further be coated with a second polymeric material. As used herein, the term "enzymes from the same batch" means enzymes that are isolated or synthesized under identical conditions, and generally are isolated or synthesized in the same isolation or synthesis procedure where the resulting enzyme composition is generally referred to as a batch. For example, a solution of enzymes is divided into two portions in which one portion of enzymes is embedded in a particle and may undergo further treatment, and the other portion of enzymes is treated differently, and these enzymes are considered to be from the same batch.

Normally, two different routes of treatment of oxalate-related disease can be employed, dependent on whether the aim of the treatment is systemic or non-systemic. Methods of the present invention provide a composition for non-systemic treatment, i.e. to provide a composition that enables reducing oxalate in the stomach in order to avoid absorption of oxalate from the gastrointestinal tract. To the best of the inventors' knowledge such a composition is novel and is based on a novel principle of, on the one hand protecting the enzyme from the acidic and enzyme-damaging environment in the stomach, and on the other hand, maintaining the enzymatic activity even in an acidic environment. This goal may be accomplished by embedding the one or more oxalate degrading enzyme in a first polymeric material, optionally coating the obtained particles with a second polymeric material, optionally cross-linking the second polymeric material and optionally reducing the cross-linked coated particles.

In one embodiment of the invention, a reduction in oxalate absorption is achieved by providing oxalate-degrading enzymes to the gastrointestinal tract, particularly the stomach. Compositions of the present invention comprise oxalate reducing enzymes including, but not limited to, oxalate oxidase, oxalate decarboxylase, oxalyl-CoA decarboxylase, or formyl-CoA transferase, or combinations thereof. These enzymes use oxalate as a substrate. Methods of the present invention comprise providing enzymatic compositions for degradation of dietary oxalate in the stomach, thus lowering the concentration of available oxalate in the stomach for absorption. This will also reduce the amount of oxalate going into the intestine for absorption in this segment of the gastrointestinal tract. In addition to absorptive pathways, oxalate secretory pathways have been recently identified in the human stomach. The compositions of the present invention would also be useful in degrading the oxalate secreted into the stomach from the circulatory system, and thus the methods of the present invention contemplate an overall reduction of the oxalate load in an individual.

In another embodiment, the present invention provides compositions and methods for the delivery of an effective amount of an oxalate reducing enzyme to the stomach of a human or animal, particularly to those who are at increased risk for oxalate-related disease. Enzyme activity is used to degrade oxalate in the stomach and reduce the amount of oxalate present in the stomach and intestinal tract, thereby reducing the amount of oxalate available for absorption. Lower levels of oxalate in the gastrointestinal tract can also lead to increased oxalate excretion from the blood into the intestines through the oxalate secretory pathways.

The compositions of the present invention are suitable for use in oxalate-related conditions including, but not limited to, hyperoxaluria, absorptive hyperoxaluria, enteric hyperoxaluria, primary hyperoxaluria, idiopathic calcium oxalate kidney stone disease (urolithiasis), vulvodynia, oxalosis associated with end-stage renal disease, cardiac conductance disorders, inflammatory bowel disease, Crohn's disease, ulcerative colitis, and patients who have undergone gastrointestinal surgery and bariatric surgery (surgery for obesity), and/or who have undergone antibiotic treatment.

A feature of a composition of the present invention is the ability of the particle to protect the oxalate-degrading enzymes from degradation by conditions such as those found in the gastric environment including, but not limited to, degradation by a protease such as pepsin or degradation due to the acidic environment.

The term "oxalate degrading enzyme" as used herein is intended to denote any enzyme that is capable of reducing oxalate. It may reduce oxalate per se and/or it may function in an oxalate reduction pathway. The present invention contemplates the use of any known oxalate reducing or degrading enzymes, and such terms "oxalate reducing" and "oxalate degrading" are used interchangeably herein.

Enzymes used in the compositions and methods of the present invention include, but are not limited to, oxalate oxidase, oxalate decarboxylase (in the present context abbreviated OxDc), oxalyl-CoA decarboxylase, or formyl-CoA transferase, or combinations thereof. Moreover, other enzymes, cofactors and co-enzymes that are substituents of oxalate degradation pathways or involved in oxalate metabolic pathways, particularly oxalate reduction, are also of relevance alone or in combination with one or more of the above-mentioned enzymes. In the present context not only the enzymes are encompassed by this definition, but also polynucleotide sequences that encode oxalate-reducing genes and proteins are contemplated by the present invention. The present invention also contemplates any binding partners of these enzymes and includes antibodies and antibody fragments that bind to or interact with the enzymes.

The enzymes may be derived by isolation from organisms, they may be purified, they may be made synthetically, semi-synthetically or by recombinant means, or they may be used as a cell lysate. Normally, the enzymes will be employed as purified recombinant protein, but since the enzymes can also be made in certain bacteria that are safe, it is also contemplated to use those bacteria as whole cells or as lysate. Due to the medical use of a composition of the invention, it is preferred that the one or more enzymes used are well-defined with respect to purity and activity. The cell lysate, if used, may be made from any microorganism that has oxalate-reducing functions, e.g. *O. formigenes*.

The compositions of the present invention may also comprise one or more additional factors which may improve the enzyme activity. These additional factors may be, e.g., oxalyl CoA, $MgCl_2$, and/or thiamine diphosphate (an active form of vitamin $B_1$).

In specific embodiments, one or more enzymes from the three main classes of oxalate-degrading enzymes are employed.

The three main classes of oxalate-degrading enzymes include the following. The first, oxalate oxidase, is expressed in higher plants and catalyzes the oxygen dependent oxidation of oxalate to $CO_2$ with concomitant formation of $H_2O_2$. This reaction forms the basis of current assays for the detection of urinary oxalate levels. A rapid three-step purification procedure has been developed to obtain oxalate oxidase from barley roots. This enzyme is also present in beetroot stem and root, amaranthus leaves, sorghum and many other grains.

Oxalate decarboxylase (EC 4.1.1.2), the second class of oxalate metabolizing enzymes, is mainly present in various fungi. It has been reported and characterized in several fungi such as, *Myrothecium verrucaria*, certain strains of *Aspergillus niger*, white rot fungus, *Coriolus versicolor* and *Collybia velutipes*. This enzyme converts oxalate to formate and carbon dioxide in an oxygen dependent reaction. Oxalate decarboxylases also have been used in the clinical assay of oxalate in blood and urine and can be used to lower oxalate levels in foods and the environment. The first bacterial oxalate decarboxylase recently has been described as the product of the YvrK gene which is expressed as a cytosolic protein in *Bacillus subtilis*. The YvrK protein (the *B. subtilis* oxalate decarboxylase) has been expressed as a functional recombinant protein in *E. coli*, purified to homogeneity and fully characterized.

The third class is the bacterial enzyme, oxalyl-CoA decarboxylase, which is active on the CoA-activated substrate and converts it into formyl-CoA. A formyl-CoA transferase then acts to exchange formate and oxalate on CoA. These enzymes have been studied in the oxalate degrading bacteria, *Pseudomonas oxalaticus* commonly found in the soil and in *Oxalobacter formigenes*, residing in the GI tract of vertebrates and humans.

The enzymes have been fully reviewed in, "The enzymes of oxalate metabolism: Unexpected structures and metabolism" Svedruzic D. et al. *Arch Biochem Biophys*. 2005 Jan. 1; 433(1):176-92, which is herein incorporated in its entirety. The enzymes, whether native enzymes, isolated proteins or those made by recombinant techniques, may be modified by recombinant or chemical means and may contain side groups or other appended molecules. For example, enzymes may be modified to have linker molecules for attachment to other molecules or chemical compounds.

In a specific embodiment of the invention, a reduction in oxalate levels is achieved by use of oxalate-degrading enzymes produced by a recombinant means, such as, e.g., *Escherichia Coli*, or other organisms which have been transformed to express oxalate-degrading enzymes.

Examples of recombinant enzymes of relevance in the present context are:
i). Oxalyl coA decarboxylase e.g. having one of the following sequences: www.expasy.org/uniprot/P40149
UniProtKB/TrEMBL entry Accession number P40149

```
                                                   SEQ.ID 1
  1 msnddnvelt dgfhvlidal kmndidtmyg vygipitnla
    rmwqddgqrf ysfrheqhag 61 yaasiagyie gkpgvcltvs apgflngvts lahattncfp
    millsgsser eivdlqqgdy 121 eemdqmnvar phckasfrin sikdipigia ravrtavsgr
    pggvyvdlpa klfgqtisve 181 eankllfkpi dpapaqipae daiaraadli knakrpviml
    gkgaayaqcd deiralveet
```

```
                                            -continued
241 gipflpmgma kgllpdnhpq saaatrafal aqcdvcylig
    arlnwlmqhg kgktwgdelk 301 kyvqidiqan emdsnqpiaa pvvgdiksav sllrkalkga
    pkadaewtga lkakvdgnka 361 klagkmtaet psgmmnysns lgvvrdfmla npdislvneg
    analdntrmi vdmlkprkrl 421 dsgtwgvmgi gmgycvaaaa vtgkpviave gdsafgfsgm
    eleticrynl pvtviimnng 481 giykgneadp qpgvisctrl trgrydmmme afggkgyvan
    tpaelkaale eavasgkpcl 541 inamidpdag vesgriksln vvskvgkk
``` www.ncbi.nlm.nih.gov/entrez/query.fcgi?db=nucleotide&cmd=search&term=M77128&doptcmdl=GenBank
GenBank Accession number M77128

```
                                                   SEQ ID 2
   1 gagcaagatg agatgtcctt cctctgtggc aatcaggaat
     atattgacgg cacgtgtttt 61 ccctacttcc ggtgtgccag acatctccaa agatctcatg
     tggttttgga atccattttt 121 gccggtatcc cggctattcc ttacttttcc aaattgggtg
     taatgcaatg aatctatggt 181 ttttaatgct gtatggacaa ttttccggca gtgaaatttt
     cagatgcatt tcatttgtat 241 tcaggcggat ttgtttaaat tgacctgaat caatattgcc
     ggattgatct aggtcaatga 301 agtcaaattg acttatgtca atggtgccaa attgacctag
     gtcaacggga tttttaaagg 361 gtatgcggca tactcggaat tgacgttaaa caacgtttat
     caaaaccaac caaagaaagg 421 tattactcat gagtaacgac gacaatgtag agttgactga
     tggctttcat gttttgatcg 481 atgccctgaa aatgaatgac atcgatacca tgtatggtgt
     tgtcggcatt cctatcacga 541 acctggctcg tatgtggcaa gatgacggtc agcgttttta
     cagcttccgt cacgaacaac 601 acgcaggtta tgcagcttct atcgccggtt acatcgaagg
     aaaacctggc gtttgcttga 661 ccgtttccgc ccctggcttc ctgaacgcg tgacttccct
     ggctcatgca accaccaact 721 gcttcccaat gatcctgttg agcggttcca gtgaacgtga
     aatcgtcgat ttgcaacagg 781 gcgattacga agaaatggat cagatgaatg ttgcacgtcc
     acactgcaaa gcttctttcc 841 gtatcaacag catcaaagac attccaatcg gtatcgctcg
     tgcagttcgc accgctgtat 901 ccggacgtcc aggtggtgtt tacgttgact tgccagcaaa
     actgttcggt cagaccattt 961 ctgtagaaga agctaacaaa ctgctcttca aaccaatcga
     tccagctccg gcacagattc 1021 ctgctgaaga cgctatcgct cgcgctgctg acctgatcaa
     gaacgccaaa cgtccagtta
```

-continued

```
1081  tcatgctggg taaaggcgct gcatacgcac aatgcgacga
      cgaaatccgc gcactggttg 1141  aagaaaccgg catcccattc ctgccaatgg gtatggctaa
      aggcctgctg cctgacaacc 1201  atccacaatc cgctgctgca acccgtgctt tcgcactggc
      acagtgtgac gtttgcgtac 1261  tgatcggcgc tcgtctgaac tggctgatgc agcacggtaa
      aggcaaaacc tggggcgacg 1321  aactgaagaa atacgttcag atcgacatcc aggctaacga
      aatggacagc aaccagccta 1381  tcgctgcacc agttgttggt gacatcaagt ccgccgtttc
      cctgctccgc aaagcactga 1441  aaggcgctcc aaaagctgac gctgaatgga ccggcgctct
      gaaagccaaa gttgacggca 1501  acaaagccaa actggctggc aagatgactg ccgaaacccc
      atccggaatg atgaactact 1561  ccaattccct gggcgttgtt cgtgacttca tgctggcaaa
      tccggatatt tccctggtta 1621  acgaaggcgc taatgcactc gacaacactc gtatgattgt
      tgacatgctg aaaccacgca 1681  aacgtcttga ctccggtacc tggggtgtta tgggtattgg
      tatgggctac tgcgttgctg 1741  cagctgctgt taccggcaaa ccggttatcg ctgttgaagg
      cgatagcgca ttcggttttct 1801  ccggtatgga actgaaaccc atctgccgtt acaacctgcc
      agttaccgtt atcatcatga 1861  acaatggtgg tatctataaa ggtaacgaag cagatccaca
      accaggcgtt atctcctgta 1921  cccgtctgac ccgtggtcgt tacgacatga tgatggaagc
      atttggcggt aaaggttatg 1981  ttgccaatac tccagcagaa ctgaaagctg ctctggaaga
      agctgttgct tccggcaaac 2041  catgcctgat caacgcgatg atcgatccag acgctggtgt
      cgaatctggc cgtatcaaga 2101  gcctgaacgt tgtaagtaaa gttggcaaga ataattagc
      ccaactttga tgaccggtta 2161  cgaccggtca cataaagtgt tcgaatgccc ttcaagttta
      cttgaagggc attttttac 2221  cttgcagttt ataaacagga aaaattgaag tattcagagc
      ggaaaagcag atttaagcca 2281  cgagaaacat tctttttat tgaaaattgc cataaacaca
      tttttaaagc tggctttttt
``` ii). Formyl Co-A transferase e.g. having the following sequence:

www.expasy.org/uniprot/O06644

UniProtKB/TrEMBL entry Accession number O06644

```
                                                SEQ ID 3
   1  mtkpldginv ldfthvqagp actqmmgflg anvikierrg
      sgdmtrgwlq dkpnvdslyf 61  tmfncnkrsi eldmktpegk elleqmikka dvmvenfgpg
      aldrmgftwe yiqelnprvi 121  lasvkgyaeg hanehlkvye nvaqcsggaa attgfwdgpp
      tvsgaalgds nsgmhlmigi
```

```
 181  laalemrhkt grgqkvavam qdavlnlvri klrdqqrler
      tgilaeypqa qpnfafdrdg 241  nplsfdnits vprggnaggg gqpgwmlkck gwetdadsyv
      yftiaanmwp qicdmidkpe 301  wkddpayntf egrvdklmdi fsfietkfad kdkfevtewa
      aqygipcgpv msmkelahdp 361  slqkvgtvve vvdeirgnhl tvgapfkfsg fqpeitrapl
      lgehtdevlk elglddakik 421  elhakqvv
``` www.ncbi.nlm.nih.gov/entrez/query.fcgi?db=nucleotide&cmd=search&term=U82167&doptcmdl=GenBank GenBank Accession number U82167

```
                                                SEQ ID 4
   1  aagcttgctt cattttgaga tgttatgcga agtgttagca
      acccaagtta gtaccttcag 61  cccctttggc gaagttttc tttcttggca gttcctttcg
      gggaaacagc cacagagaat 121  aaaaaccaaa agttgtacca acgacaagga aatgagaaat
      tatgactaaa ccattagatg 181  gaattaatgt gcttgacttt acccacgtcc aggcaggtcc
      tgcctgtaca cagatgatgg 241  gtttcttggg cgcaaacgtc atcaagattg aaagacgtgg
      ttccggagat atgactcgtg 301  gatggctgca ggacaaacca aatgttgatt ccctgtattt
      cacgatgttc aactgtaaca 361  aacgttcgat tgaactggac atgaaaaccc ggaaggcaa
      agagcttctg gaacagatga 421  tcaagaaagc cgacgtcatg gtcgaaaact cggaccagg
      cgcactggac cgtatgggct 481  ttacttggga atacattcag gaactgaatc cacgcgtcat
      tctggcttcc gttaaaggct 541  atgcagaagg ccacgccaac gaacacctga agtttatga
      aaacgttgca cagtgttccg 601  gcggtgctgc agctaccacc ggtttctggg atggtcctcc
      aaccgtttcc ggcgctgctc 661  tgggtgactc caactccggt atgcacctga tgatcggtat
      tctggccgct ctggaaatgc 721  gtcacaaaac cggccgtggt cagaaagttg ccgtcgctat
      gcaggacgct gttctgaatc 781  tggttcgtat caaactgcgt gaccagcaac gtctggaaag
      aaccggcatt ctggctgaat 841  acccacaggc tcagcctaac tttgccttcg acagagacgg
      taacccactg tccttcgaca 901  acatcacttc cgttccacgt ggtggtaacg caggtggcgg
      cggccagcca ggctggatgc 961  tgaaatgtaa aggttgggaa accgatgcgg actcctacgt
      ttacttcacc atcgctgcaa 1021  acatgtggcc acagatctgc gacatgatcg acaagccaga
      atggaaagac gacccagcct 1081  acaacacatt cgaaggtcgt gttgacaagc tgatggacat
      cttctccttc atcgaaacca
```

-continued

```
1141  agttcgctga caaggacaaa ttcgaagtta ccgaatgggc
      tgcccagtac ggcattcctt 1201  gcggtccggt catgtccatg aaagaactgg ctcacgatcc
      ttccctgcag aaagttggta 1261  ccgtcgttga agttgtcgac gaaattcgtg gtaaccacct
      gaccgttggc gcaccgttca 1321  aattctccgg attccagccg gaaattaccc gtgctccgct
      gttgggcgaa cataccgacg 1381  aagttctgaa agaactgggt cttgacgatg ccaagatcaa
      ggaactgcat gcaaaacagg 1441  tagtttgatc cgtcagactt tctgggcaaa acggcactct
      ccggagtgcc gttttttgt 1501  cacacgaaac cctaatcaaa caagcacgtg caatgattcc
      acatcattgc ggccacattc 1561  atccttcggg tcattactg
``` iii). Oxalate decarboxylase e.g. having the following sequence
www.expasy.org/uniprot/O34714
UniProtKB/TrEMBL entry Accession number O34714

```
                                                SEQ ID 5
  1  mkkqndipqp irgdkgatvk iprnierdrq npdmlvppet
     dhgtvsnmkf sfsdthnrle 61  kggyarevtv relpisenla svnmrlkpga irelhwhkea
     ewaymiygsa rvtivdekgr 121  sfiddvgegd lwyfpsglph siqaleegae fllvfddgsf
     senstfqltd wlahtpkevi 181  aanfgvtkee isnlpgkeky ifenqlpgsl kddivegpng
     evpypftyrl leqepieseg 241  gkvyiadstn fkvsktiasa lvtvepgamr elhwhpnthe
     wqyyisgkar mtvfasdgha 301  rtfnyqagdv gyvpfamghy venigdeplv fleifkddhy
     advslnqwla mlpetfyqah 361  ldlgkdftdv lskekhpvvk kkcsk
``` www.ebi.ac.uk/cgi-bin/
dbfetch?db=emblcds&id=CAA11727
CoDing Sequence Accession number AJ223978

```
                                                SEQ ID 6
  1  atgaaaaaac aaaatgacat tccgcagcca attagaggag
     acaaaggagc aacggtaaaa 61  atcccgcgca atattgaaag agaccggcaa aaccctgata
     tgctcgttcc gcctgaaacc 121  gatcatggca ccgtcagcaa tatgaagttt tcattctctg
     atactcataa ccgattagaa 181  aaaggcggat atgcccggga agtgacagta cgtgaattgc
     cgatttcaga aaaccttgca 241  tccgtaaata tgcggctgaa gccaggcgcg attcgcgagc
     ttcactggca taaagaagct 301  gaatgggctt atatgattta cggaagtgca agagtcacaa
     ttgtagatga aaaagggcgc 361  agctttattg acgatgtagg tgaaggagac ctttggtact
     tcccgtcagg cctgccgcac
```

```
421  tccatccaag cgctggagga gggagctgag ttcctgctcg
     tgtttgacga tggatcattc 481  tctgaaaaca gcacgttcca gctgacagat tggctggccc
     acactccaaa agaagtcatt 541  gctgcgaact tcggcgtgac aaaagaagag atttccaatt
     tgcctggcaa agaaaaatat 601  atatttgaaa accaacttcc tggcagttta aaagatgata
     ttgtggaagg gccgaatggc 661  gaagtgcctt atccatttac ttaccgcctt cttgaacaag
     agccgatcga atctgaggga 721  ggaaaagtat acattgcaga ttcgacaaac ttcaaagtgt
     ctaaaaccat cgcatcagcg 781  ctcgtaacag tagaacccgg cgccatgaga gaactgcact
     ggcacccgaa tacccacgaa 841  tggcaatact acatctccgg taaagctaga atgaccgttt
     ttgcatctga cggccatgcc 901  agaacgttta attaccaagc cggtgatgtc ggatatgtac
     catttgcaat gggtcattac 961  gttgaaaaca tcggggatga accgcttgtc tttttagaaa
     tcttcaaaga cgaccattat 1021 gctgatgtat ctttaaacca atggcttgcc atgcttcctg
     aaacatttgt tcaagcgcac 1081 cttgacttgg gcaaagactt tactgatgtg ctttcaaaag
     aaaagcaccc agtagtgaaa 1141 aagaaatgca gtaaataa
``` and/or
iv) Oxalate oxidase e.g. having the following sequence
www.expasy.org/uniprot/O24004
UniProtKB/TrEMBL entry Accession number O24004

```
                                                SEQ ID 7
  1  mgysknlgag lftmlllapa imatdpdplq dfcvadldgk
     avsvnghtck pmseagddfl 61  fsskltkagn tstpngsavt eldvaewpgt ntlgvsmnrv
     dfapggtnpp hihprateig 121  mvmkgellvg ilgsfdsgnk lysrvvrage tfviprglmh
     fqfnvgktea ymvvsfnsqn 181  pgivfvpltl fgsnppiptp vltkalrvea gvvellkskf
     aggs
``` www.ncbi.nlm.nih.gov/entrez/
query.fcgi?db=nucleotide&cmd=search&term=Y14
203&doptcmdl=GenBank
GenBank Accession number Y14203

```
                                                SEQ ID 8
  1  agcttagcag caaccaccag tagtgcctca aaggctcctg
     atcaacaaac tctagctcat 61  cagtggtagc taagcttgct acatagcaag caatgggtta
     ctctaaaaac ctaggggctg 121  gcctgttcac catgctgctc cttgctccgg ccatcatggc
     taccgaccct gaccctctac 181  aggacttctg cgtcgcggac ctcgatggca aggcggtctc
     ggtgaacggg catacgtgta
```

-continued

```
241 agcccatgtc ggaggccggc gacgacttcc tcttctcgtc
    caagctgacc aaggccggca 301 acacgtccac cccgaacggc tcggccgtga cggagctcga
    cgtggccgag tggcccggta 361 cgaacacgct gggcgtgtcc atgaaccgtg tggacttcgc
    gccgggcggc accaacccgc 421 cgcacatcca cccgcgtgca accgagatcg gcatggtgat
    gaaaggtgag ctcctcgttg 481 gaatcctcgg cagctttgac tccggaaaca agctctactc
    cagggtggtg cgtgccggag 541 agactttcgt catcccgcgc ggcctcatgc acttccagtt
    caacgttggt aagacggaag 601 cctacatggt tgtgtccttc aacagccaga accctggcat
    cgtcttcgtg ccgctcacac 661 tcttcggttc caacccgccc atccccacac cggtgctcac
    caaggctctt cgggtggagg 721 ccggggtcgt ggaacttctc aagtccaagt tcgccggtgg
    gtcttaactt ccatgagccc 781 caaatgatca atatgaatat gtaattctat atatccatgt
    atgctgcgaa tttaatagta 841 ctcgacagga gactatattc aagcttctgg ataagctcgc
    atttcatagt aataagattg 901 aataagttat cctagcggtt cagccttcag aaccaatgcg
    aggacttaaa atgtattgct 961 tcttattatt
```

DNA sequences encoding oxalate-degrading enzymes are known to those skilled in the art and are described in, e.g. WO 98/16632, which is incorporated herein in its entirety.

Additionally, a composition according to the present invention may comprise enzymes that comprise modifications or mutations, including, but not limited to, chimeras formed using domains comprising the oxalate degrading active site of an oxalate reducing enzyme, or peptide fragments, notably those comprising or consisting of the active sites; modifications or mutations, including, but not limited to, deletions, insertions, replacements, reversions, mutations for increased activity, substitution of naturally occurring amino acids with non-natural amino acids, or other modifications known to those skilled in the art. Such modified enzymes may have more, less or the same activity as native enzymes, or may have characteristics that are the same or different from native or unmodified enzymes. The present invention contemplates methods and compositions comprising whole enzymes, fragments, peptides, binding regions, active sites or other functional regions, segments, sequences and promoter and control sequences of oxalate reducing enzymes.

In one example, an oxalate decarboxylase was modified. In total, 7 genes were created from the original yvrk gene sequence (the wild-type yvrk). The original gene was from *Bacillus subtilis*, the gene sequence was optimized for expression in *E. coli* using an algorithm from GenScript Corporation, Piscataway, N.J. The gene was optimized for codon usage, balancing GC content, removing repetitive elements, and ensuring the absence of internal restriction sites for cloning. The codon optimized gene resulted in a protein with the identical amino acid sequence as the wild-type yvrk.

Modifications were then made to the single cysteine codon of both the wild-type yvrk gene, and the optimized yvrk gene, resulting in 6 additional unique gene sequences. The cysteine codons were modified to serine, arginine, or alanine codons. The modifications were performed for the purposes of eliminating disulfide bonding, and modifying the secondary and tertiary structure of the enzyme.

The gene sequence of the wild-type yvrk gene may be optimized for additional expression systems such as *Pichia* or *Saccharomyces* using the same methods. In addition, expression in a *Bacillus* expression system may be improved by optimizing the gene for optimum codon usage and GC content, and removal of repetitive elements. Codon optimization may also be used for modification of the secondary structure of the protein at positions other than the cysteine codon already modified, or in addition to the cysteine modification, for example, as a method to improve pegylation, microsphere binding or encapsulation, as a method to improve pH stability at low pHs, or as a method to improve the activity of the protein.

Original yvrk sequence with the cysteine codon marked in bold.

SEQ ID 9

```
AAAAAACAAAATGACATTCCGCAGCCAATTAGAGGAGACAAAGGAGCAACGGTAAAAATC
CCGCGCAATATTGAAAGAGACCGGCAAAACCCTGATATGCTCGTTCCGCCTGAAACCGAT
CATGGCACCGTCAGCAATATGAAGTTTTCATTCTCTGATACTCATAACCGATTAGAAAAA
GGCGGATATGCCCGGGAAGTGACAGTACGTGAATTGCCGATTTCAGAAAACCTTGCATCC
GTAAATATGCGGCTGAAGCCAGGCGCGATTCGCGAGCTTCACTGGCATAAAGAAGCTGAA
TGGGCTTATATGATTTACGGAAGTGCAAGAGTCACAATTGTAGATGAAAAAGGGCGCAGC
TTTATTGACGATGTAGGTGAAGGAGACCTTTGGTACTTCCCGTCAGGCCTGCCGCACTCC
ATCCAAGCGCTGGAGGAGGGAGCTGAGTTCCTGCTCGTGTTTGACGATGGATCATTCTCT
GAAAACAGCACGTTCCAGCTGACAGATTGGCTGGCCCACACTCCAAAAGAAGTCATTGCT
GCGAACTTCGGCGTGACAAAAGAAGAGATTTCCAATTTGCCTGGCAAAGAAAAATATATA
TTTGAAAACCAACTTCCTGGCAGTTTAAAAGATGATATTGTGGAAGGGCCGAATGGCGAA
GTGCCTTATCCATTTACTTACCGCCTTCTTGAACAAGAGCCGATCGAATCTGAGGGAGGA
AAAGTATACATTGCAGATTCGACAAACTTCAAAGTGTCTAAAACCATCGCATCAGCGCTC
```

-continued

GTAACAGTAGAACCCGGCGCCATGAGAGAACTGCACTGGCACCCGAATACCCACGAATGG

CAATACTACATCTCCGGTAAAGCTAGAATGACCGTTTTTGCATCTGACGGCCATGCCAGA

ACGTTTAATTACCAAGCCGGTGATGTCGGATATGTACCATTTGCAATGGGTCATTACGTT

GAAAACATCGGGGATGAACCGCTTGTCTTTTTAGAAATCTTCAAAGACGACCATTATGCT

GATGTATCTTTAAACCAATGGCTTGCCATGCTTCCTGAAACATTTGTTCAAGCGCACCTT

GACTTGGGCAAAGACTTTACTGATGTGCTTTCAAAAGAAAAGCACCCAGTAGTGAAAAAG

AAATGCAGTAAA

Yvrk gene sequence optimized for *E. coli*, with restriction sites at the 5' and 3' ends (underlined), and the cysteine codon marked in bold.

SEQ ID 10

<u>CATATG</u>AAAAAACAGAATGACATTCCACAGCCGATTCGCGGCGATAAAGGCGCGACCGTC

AAAATTCCTCGCAATATCGAACGCGACCGCCAGAATCCGGATATGCTGGTGCCGCCGGAG

ACGGACCATGGCACGGTGTCTAACATGAAATTCTCTTTTAGCGATACCCACAACCGCCTG

GAAAAAGGTGGCTACGCGCGCGAGGTTACCGTCCGTGAACTGCCAATTAGCGAAAATCTG

GCTTCGGTTAACATGCGTCTGAAACCAGGTGCTATCCGTGAGCTGCACTGGCACAAGGAA

GCGGAATGGGCGTATATGATTTACGGTTCAGCACGTGTTACCATCGTAGACGAGAAAGGT

CGTAGCTTTATCGATGATGTTGGCGAAGGTGATCTGTGGTATTTCCCATCTGGCCTGCCG

CATTCGATTCAGGCGCTGGAAGAAGGCGCTGAATTTCTGCTGGTGTTCGATGATGGTTCC

TTTTCTGAAAACAGCACGTTCCAGCTGACGGATTGGCTGGCGCACACGCCGAAAGAAGTC

ATTGCGGCCAATTTTGGGGTAACCAAAGAAGAAATTTCCAACCTGCCGGGCAAAGAAAAG

TATATTTTTGAGAATCAGCTGCCGGGCTCTCTGAAGGACGATATTGTAGAAGGCCCTAAC

GGTGAGGTGCCGTATCCGTTCACCTATCGTCTGCTGGAGCAGGAACCGATTGAAAGCGAA

GGCGGTAAAGTTTATATCGCAGATTCCACTAACTTTAAAGTCTCCAAGACCATTGCCAGC

GCCCTGGTCACCGTGGAACCGGGAGCGATGCGCGAGCTGCACTGGCATCCGAACACGCAC

GAATGGCAGTATTATATTTCCGGCAAAGCACGCATGACCGTTTTTGCCTCAGATGGACAC

GCTCGCACGTTTAATTATCAAGCGGGTGATGTTGGCTACGTTCCTTTCGCCATGGGCCAT

TATGTAGAAAATATCGGCGATGAACCACTGGTGTTTCTGGAGATCTTTAAAGATGACCAC

TATGCCGATGTTTCACTGAATCAGTGGCTGGCCATGCTGCCGGAAACTTTTGTTCAGGCG

CATCTGGACCTGGGTAAAGACTTTACGGATGTGCTGAGCAAAGAAAAACACCCGGTAGTC

AAGAAGAAATGCAGTAAA<u>GGATCC</u>

The oxalate-degrading enzyme is normally present in a composition of the invention in an amount that is sufficient to degrade substantially all oxalate normally present in a standard meal. Depending on the food choices, an average Western diet can contain 100 to 300 mg of oxalate/day. In general, about 0.2 g of the particles comprising enzyme (equal to 20 mg of OxDc in 1 mL of suspension of particles) can remove 180 mg oxalate in simulated gastric conditions within 30 min.

An effective amount comprises an amount of activity units of oxalate-reducing enzyme activity that will reduce a portion of the oxalate present, or a level of activity units of oxalate-reducing enzyme activity that will initiate a reduction in the amount of oxalate or maintain a lowered amount of oxalate in the individual, compared to the amount of oxalate present before administration of the composition. The number of activity units of oxalate-reducing enzyme activity that can be used in a single dose composition can range from about 0.0001 units to about 5,000 units, from about 5 units to 100 units, from 0.05 to 50 units, to 0.5 to 500, from about 0.01 units to about 50 units, from about 0.01 units to about 5 units, from about 1 units to about 100 units, from about 25 units to about 50 units, from about 30 units to about 100 units, from about 40 units to about 120 units, from about 60 units to about 15 units to about 50 units to about 100 units, from about 100 units to about 500 units, from about 100 units to about 300 units, from about 100 units to about 400 units, from about 100 units to about 5,000 units, from about 1,000 units to about 5,000 units, from about 2,500 units to about 5,000 units, from about 0.001 units to about 2,000 units and all ranges encompassed therein. A unit of the enzyme is the amount of enzyme that will degrade one micromole of oxalate per minute at 37° C.

A composition of the present invention comprises a particle comprising an oxalate-degrading enzyme embedded in a first polymeric material. In the non-limiting examples herein are described methods of how to embed the enzyme in the first polymeric material. A person skilled in the art may find other methods suitable for use in order to prepare a composition according to the present invention. By incorporation of the enzyme in the first polymeric material, the enzyme obtains a certain protection against conditions similar to gastric fluid with respect to pH and pepsin. The resulting embedded enzyme composition appears as particles, i.e. discrete units in micron- or nano-size. Accordingly, the terms "particles", "microparticles" and "nanoparticles" are used herein to describe compositions containing one or more kinds of an oxalate-reducing enzyme embedded in a first polymer or in a first and a second polymer. In general the term "particles" are used as the broadest term, i.e. without any specific size or shape attribution, whereas the term "microparticles" is used when the particles obtained have mean particle sizes in the range of 1 μm to 1000 μm. Likewise, the term "nanoparticles" is used herein when the particles obtained have mean particle sizes ranging from 1 nm to 1000 nm. As used herein the singular of the term "an enzyme" refers to multiple copies of the enzyme molecule, as is commonly understood in reference to protein molecules. As used herein, the term "one or more enzymes" means that one type of enzyme may be present, such as formyl-CoA transferase is intended, or more than one type of enzyme, such as a composition comprising, for example oxalyl CoA decarboxylase and formyl CoA transferase; oxalate decarboxylase and oxalate oxidase, or a combination of wild-type enzyme and mutant enzyme, are present in the composition.

Normally, the particles of a composition of the invention have an average diameter of from about 50 nm to about 1 mm, such as, e.g., from about 500 nm to about 500 μm, from about 1 μm to about 500 μm, from about 2 μm to about 100 μm, from about 4 μm to about 80 μm, from about 6 μm to about 60 μm, from about 8 μm to about 40 μm, from about 10 μm to about 20 μm.

The term "embedded" as used herein is intended to denote that the enzyme is admixed or contacted with the first polymeric material in such a way that i) the first polymeric material substantially envelopes the enzyme, i.e. the particle can be regarded as an enzyme-containing core surrounded by the first polymeric material; the core may contain other substances than the enzymes such as, e.g., a part of the polymeric material as well, or ii) the enzymes is incorporated in the first polymeric material in such a manner that the major part of the surface of the particles is composed of the first polymeric material, but a minor part of the enzyme may as well appear on the surface of the particles. In general, it is contemplated that at least 50% of the outer surface of the particles is composed of the first polymeric material and at the most about 20% by weight of the enzyme present in the particles may be present on the outer surface of the particles, and/or iii) the enzyme is substantially homogeneously distributed in the first polymeric material.

Thus, in a composition of the invention the oxalate-degrading enzyme is protected from the (gastric) environment. Furthermore, the composition of the invention does not substantially release the enzyme to the (gastric) environment. In other words, the enzyme remains in the composition after oral administration for a sufficient period of time to enable oxalate in the stomach to be degraded. In a composition, a first polymeric material may function as a protective carrier for the enzyme and at the same time may allow the substrate, i.e. oxalate, to diffuse or otherwise be transported into the composition to enable an in situ degradation of oxalate. A feature of a composition of the present invention is the composition's ability to retain the enzymatic activity for a period of time longer than that observed for an enzyme that is not embedded in a polymeric matrix, especially under acidic conditions. Accordingly, one aspect the present invention comprises a composition comprising particles comprising one or more oxalate degrading enzymes embedded in a first polymeric material, wherein the embedded enzyme retains at least two times the activity of the one or more non-embedded free enzymes, obtained from the same batch, upon incubation in USP simulated gastric juice containing 84 mM HCl and 3.2 mg/ml pepsin at pH>1, e.g. in a range of pH about 1 to pH about 5, such as, e.g., from pH about 2 to pH about 5, from pH about 2.5 to pH about 4.5, from pH about 2.5 to pH about 3.5 such as pH about 3 at 37° C. for at least 60 minutes. It is important that the test conditions for the composition according to the invention and the free enzymes are the same, for example, with respect to the nature and purity of the enzyme, the initial concentration of the enzyme, the test volume, the composition of the incubation medium (e.g. simulated gastric juice or fluid), the temperature etc.

Normally, the embedded enzyme retains at least three times the activity, at least four times the activity, or at least five times the activity of the one or more non-embedded free enzymes obtained from the same batch upon incubation in USP simulated gastric juice containing 84 mM HCl and 3.2 mg/ml pepsin at pH>1, e.g. in a range of pH about 1 to pH about 5, from pH about 2 to pH about 5, from pH about 2.5 to pH about 4.5, from pH about 2.5 to pH about 3.5 such as pH about 3, at 37° C. for at least 30 minutes, at least 45 min, at least 60 minutes, at least 75 minutes, at least 90 minutes, at least 105 minutes or at least 120 minutes.

In a specific embodiment, the one or more embedded oxalate degrading enzymes in a composition of the invention retain at least two times, at least 10 times, at least 50 times or at least 100 times, the activity of the one or more non-embedded free enzyme, obtained from the same batch, upon incubation in 84 mM HCl and 3.2 mg/ml pepsin at pH>1, e.g. in a range of pH about 1 to pH about 5, from pH about 2 to pH about 5, from pH about 2.5 to pH about 4.5, from pH about 2.5 to pH about 3.5 such as pH about 3, at 37° C. for at least 60 minutes.

Simulated gastric juice (gastric fluid) referred to above is described in USP (United States Pharmacopoeia) and contains pepsin and has a specific ratio of concentrated HCl. (USP simulated gastric juice contains 2 g NaCl, 3.2 g pepsin and 7 mL concentrated HCl in 1 L volume. The pH of this solution usually ranged from 1.2 to 1.5, depending on the concentration of the HCl used. In some examples herein, the pH was adjusted to above 2. This may be the case when microparticles without any coating were employed. For the present purpose, the pH should be in the acid range, i.e. at the most about 7, at the most 6 and the pH range should normally be from about 1 to about 5, from about 2 to about 5. In the experimental section herein are more details relating to the above-mentioned test and to determination of the enzymatic activity.

The residence time in the stomach of a human is on average about 120 min. It is contemplated that the enzymatic activity of the compositions of the present invention is retained at a sufficient level, an effective level, for 120 min or more. From the examples herein it is seen that it is possible to retain at least 50% of the enzymatic activity for a composition according to the invention after 120 min of exposure to an acidic environment. If the enzyme that is used is not embedded in a polymer, e.g., a non-embedded enzyme, the activity decline is very rapid, and no activity is left after 60 min in acidic environment.

Normally, the activity of one or more oxalate degrading enzymes in a composition according to the invention at the most decreases to about 30%, at the most decreases to 40% such as at the most decreases to about 50%, at the most decreases to about 60% or at the most decreases to about 70%, when incubated in an aqueous buffer solution having a pH in the range of from about 1.0 to about 5, in a range of from about 1.0 to about 4.5, from about 1.5 to about 4.5, from about 2.0 to about 4.0 or from about 2.2 to about 4.0, for about 60 min. for about 90 min, for about 105 minutes or for about 120 minutes, with the initial activity being set to 100%.

In a specific embodiment, the activity of the oxalate degrading enzyme in a composition of the present invention at the most decreases to 80%, with the initial activity being set to 100%, when tested at a pH of from about 2.0 to about 4.0 for a time period of 60 min.

In a further specific embodiment, the activity of one or more oxalate degrading enzymes in a composition of the present invention at the most decreases to about 20% when incubated in an aqueous buffer solution having a pH in the range of from about 2 to about 4.5 for 2 hours, and the initial activity being set to 100%. Notably, the activity at the most decreases to 30%, and the initial activity being set to 100%.

Suitable buffer substances for providing a buffer solution having a specific pH are known to persons skilled in the art. Examples are glycine buffers (pH 2-3), acetate buffers, phosphate buffers, borate buffers and the like. The buffer solution may contain additional ingredients such as e.g. inorganic salt in order to adjust the ionic strength of the buffer solution, or one or more proteases like e.g. pepsin in order to ensure that the conditions in the buffer solutions challenge whether the embedded enzyme can withstand such harsh conditions. In the event that one or more proteases are included, the concentration thereof is normally at the same level as that used in USP simulated gastric juice.

As mentioned herein before, the oxalate degrading enzymes can be of various types, classes, identity and nature. In a preferred aspect, a composition of the present invention comprises one or more oxalate degrading enzymes including oxalate decarboxylase, oxalate oxidase, or a combination of oxalyl-CoA decarboxylase and formyl CoA transferase, or combination thereof.

Suitable polymeric materials for use as a first polymeric material in a composition of the present invention, include, but are not limited to, man-made or natural polymers, including, but not limited to, i) a polysaccharide: alginate including alginic acid, alginate e.g. sodium alginate, potassium alginate, ammonium alginate, calcium alginate, propane-1,2-diol alginate, acacia, carrageenan, chitosan and its derivatives, chondroitin sulfate, dextran derivatives, heparin, hyaluronic acid, inulin, a cellulose or a cellulose derivative including methylcellulose, carboxymethylcellulose, sodium carboxymethylcellulose, hydroxypropylcellulose, hydroxypropylmethylcellulose, ethylmethylcellulose, or the like or combinations thereof; ii) a mucopolysaccharide, iii) a gum including locust bean gum, guar gum, tragacanth, agar, acacia gum, xanthan gum, karaya gum, tara gum, gellan gum, or the like or combinations thereof; iv) a gelling- or swelling agent including hydrocolloids and hydrogelling agents such as, agar, carrageenan, gelatin, polyvinylpyrrolidone, or the like, or combinations thereof; v) others like e.g. protein and polyamide: collagen, albumin, protamine, spermine, synthetic polymer: poly (acrylic acid), poly amino acids (polylysine, etc), polyphosphoric acid, tripolyphosphate, poly (L-lactic acid), poly (vinyl alcohol), poly (DL-lactic acid-co-glycolic acid), or mixtures and combinations thereof.

In specific embodiments the first polymeric material is chitosan, alginate, pectin or hyaluronic acid. In more specific embodiments, the first polymeric material is chitosan or alginate.

Other polymeric materials may be biopolymers or synthetic polymers. Examples of biopolymers include, but are not limited to, proteins, polysaccharides, mucopolysaccharides, heparin, heparin sulfate, heparinoids, dermatan sulfate, pentosan polysulfate, chondroitin sulfate, cellulose, agarose, chitin, carrageenin, linoleic acid, and allantoin, cross-linked collagen, fibronectin, laminin, elastin, cross-linked elastin, collagen, gelatin, hyaluronic acid, chitosan alginate, dextran, methylcellulose, polylysine, and natural rubber. In the compositions of the present invention wherein polymeric matrices are formed, these matrices are porous such that small water soluble molecules can enter and exit the polymeric matrix, including, but not limited to molecules such as oxalate, formic acid, formate, carbon dioxide, oxygen, or oxalyl-CoA. A concentration of the first polymeric material in a composition of the invention is normally in a range from 20% to 70% of the total dry materials.

In addition to the one or more enzymes and the first polymeric material, the particles may also contain one or more additives such as, e.g., pH adjusting agents, buffering agents, solubilizing agents, stabilizers, preservatives, cofactors for the enzymes or one or more pharmaceutically acceptable excipients such as, e.g. fillers, diluents, carriers or the like.

Moreover, it may be advantageous to create a localized acidic pH environment around a protein when the physiological conditions result in a pH well above the reasonable working range of the enzyme. For example, in a higher pH location, an oxalate degrading protein with maximum activity at pH three would benefit from a delivery vehicle capable of reducing the local pH in the proximity around the enzyme to around three.

One method for reducing the local pH is to incorporate a polymer that can undergo hydrolytic degradation in physiological conditions to produce acidic products that reduce the localized pH. For example, alpha polyesters such as PLA, PGA and PLGA biodegrade hydrolytically in vivo to form organic acids (lactic acid and glycolic acid) which can drive down the pH locally into to a functionally desirable range for the enzyme. Poly(dl-lactide) (DLPLA) is an amorphous polymer exhibiting a random distribution of both isomeric forms of lactic acid that can degrade quickly.

In addition, it may be desirable to include a buffer in the delivery vehicle in the form of a base, base containing or base generating material that works in conjunction with the in vivo pH, or the localized pH, or a combination of both to optimize/control the local pH around the enzyme. These buffers may include salts of organic or inorganic compounds or a number of other buffers. It is understood that the pKa of the conjugate acids of which the buffering materials are associated/derived from can be utilized in the appropriate selection of buffering materials.

The particles may be subjected to a cross-linking procedure. Such a cross-linking procedure may strengthen the properties of the particles such as to avoid loss of enzymatic activity by negative impact of pH or pepsin from the surroundings during storage or after oral administration, or to reduce release of the enzyme from the particles or to reduce or prevent migration of the enzyme towards the surface of the particles. The cross-linking procedures and suitable material for use in such a procedure are described herein.

The particles of the invention may be constructed of polymers that are cross-linked by physical or chemical cross-linking. Physical cross-linking may comprise opposite charged polymers cross-linked with each other by salt bonds (for example: chitosan, which is positively charged, cross-links with tripolyphosphate or heparin, which are negatively charged polymers), charged polymers cross-link with opposite charged ions (for example: alginate with $Ca^{2+}$, carboxymethyl-cellulose with $Al^{3+}$). The term "physical cross-linking" used in the present context also includes non-covalent bindings and/or interactions.

Chemical cross-linking generally comprises cross linking by cross-linkers with two reactive functional groups such as by polymer bearing amine groups such as proteins, polyamide, chitosan and its derivatives, may be cross-linked through glutaraldehyde or genipin. UV irradiation can be used to induce polymers bearing light sensitive groups to form covalent cross-links.

Methods for preparation of nano- and micro-particles are known in the art and include emulsion, coacervation/precipitation, spray-drying techniques and others. The properties of nanoparticles or microparticles (for examples: micro-environmental buffer capacity, mechanical strength, particle size, oxalate diffusion rate, interactions with enzymes) largely depend on selected polymer(s), polymer composition and ratio, cross-linking method and preparation procedure. More than one type of cross-linking may be utilized in the microparticles of the invention (e.g. chemical cross-linking as well as physical cross-linking, see the examples herein).

In a specific embodiment the first polymeric material is cross-linked to itself and/or to the one or more enzymes embedded in the first polymeric material.

In a composition of the invention, such as a composition wherein the first polymeric material is cross-linked to itself and/or the enzymes embedded therein, the level of retained enzymatic activity upon incubation in 84 mM HCl and 3.2 mg/ml pepsin at pH>1, e.g. in a range of pH about 1 to pH about 5, from pH about 2 to pH about 5, from pH about 2.5 to pH about 4.5, from pH about 2.5 to pH about 3.5 for pH about 3, at 37° C. for at least 30 minutes, for at least 60 minutes, for at least for at least 80 minutes, for at least 100 minutes, for at least 120 minutes, for at least 140 minutes, for at least 160 minutes, for at least 180 minutes, for at least 200 minutes, for at least 220 minutes, or at for least 240 minutes is increased by a factor of at least 2, at least 5, at least 10, at least 15, at least 20, at least 50 or at least 100 as compared to compositions of enzymes of the same batch embedded in the polymer but without the polymer being cross-linked or the enzymes and polymer being cross-linked; or compared to the same batch of free enzymes.

The particles, optionally the particles wherein at least a part of the first polymeric material is cross-linked, may also be provided with a coating. Such a coating has generally the same function as the first polymer, i.e. to avoid a substantial decrease in the enzymatic activity of the enzyme embedded in the first polymer during storage and/or after oral administration.

Accordingly, in a specific embodiment, the particles are coated with a second polymeric material. Suitable coating materials are such materials that allow an aqueous composition containing oxalate to diffuse into, or otherwise enter, the particle of the invention. As mentioned above, the substrate (i.e. the oxalate-containing medium) enters into the particle composition of the invention so that enzymatic degradation of oxalate can occur. Accordingly, coating materials resulting in either diffusion coating or otherwise permeable coatings (e.g. coatings containing pore-forming substances that are substantially water-soluble) can be applied.

Examples of suitable coating materials include, but are not limited to, the materials contemplated as first polymeric materials. A coating material may be chosen that is different than that used as a first polymeric material, but the first polymeric material and the coating material may also be the same. Specific examples of coating materials are film-forming agents such as, e.g. polyvinylpyrrolidone, hydroxypropylmethylcellulose (HPMC), hydroxyethylcellulose, hydroxypropylcellulose, polydextrose, maltodextrin, or other polysaccharides including chitosan, alginates and hyaluronic acid. In specific embodiments, the coating material, if present, is one that can be subjected to cross-linking such as, e.g., chitosan and alginate.

In a specific embodiment the first and/or second polymeric material is a polysaccharide such as chitosan, alginate, pectin or hyaluronic acid. The first and second polymeric materials may be the same or different.

Normally, the polymer percentage of the first and, if present, second polymer material is from about 10% to about 80%, from about 60% to about 80% of the total dry material of a particle.

If present, the coating material is normally applied in such an amount the weight gain of the particles is at the most about 40%. As seen from the examples herein, the concentration of the coating material in a particle composition is normally at the most 25% w/w such as at the most about 20% w/w, at the most about 15% w/w or at the most about 10%. A particle having a coating is referred to herein as a coated composition.

In a composition of the invention, such as in a coated composition of the invention, the level of retained enzymatic activity upon incubation in 84 mM HCl and 3.2 mg/ml pepsin at pH>1, e.g. in a range of pH about 1 to pH about 5, from pH about 2 to pH about 5, from pH about 2.5 to pH about 4.5, from pH about 2.5 to pH about 3.5, such as pH about 3, at 37° C. for at least 60 minutes, for at least for at least 80 minutes, for at least 100 minutes, for at least 120 minutes, for at least 140 minutes, for at least 160 minutes, for at least 180 minutes, for at least 200 minutes, for at least 220 minutes, or at for least 240 minutes is increased by a factor of at least 2, at least 10, at least 50 or at least 100 as compared to compositions of the same batch of enzymes embedded in particles lacking a coating, or compared to the same batch of free enzymes.

As mentioned above and as shown in the Examples herein, the stability of the enzymatic activity of the oxalate-degrading enzyme in a composition of the invention may be further improved by employing coated particles wherein the coating has been subjected to cross-linking. Cross-linking of a polymeric material is well-known in the art and may be performed by physical cross-linking or by use of a chemical cross-linking agent.

Suitable chemical cross-linking agents for use in this context include, but are not limited to, dialdehyde, 1-ethyl-3[3-dimethylaminopropyl]carbodiimide (EDC), disuccinimidyl suberate (DSS) or (N-[p-maleimidophenyl]isocyanate (PMPI). In a specific embodiment, the cross-linking agent is a dialdehyde, notably glutaraldehyde or glyoxal. In an embodiment, the cross-linking agent is glutaraldehyde. The cross-linking is normally carried out in 1-5% gluteraldehyde in 50 mM phosphate buffer, pH 7.5 at 37° C., shaking for 1-2 hours.

As mentioned above, a feature of a composition of the invention is that the first and, if present, second polymeric material is permeable for small molecules to allow the substrates for and products of the reaction catalyzed by the one or more enzymes to diffuse through said polymeric materials. Moreover, the first and/or second polymeric materials remain substantially intact upon incubation in 84 mM HCl and 3.2 mg/ml pepsin at pH>1, e.g. in a range of pH about 1 to pH about 5, from pH about 2 to pH about 5, from pH about 2.5 to pH about 4.5, from pH about 2.5 to pH about 3.5 such as pH about 3, at 37° C. for at least 60 minutes, for at least 80 minutes, for at least 100 minutes, for at least 120 minutes, for at least 140 minutes, for at least 160 minutes, for at least 180 minutes, for at least 200 minutes, for at least 220 minutes, or for at least 240 minutes.

In another embodiment the first and/or second polymeric materials are cross-linked to themselves and/or each other and/or to the one or more enzymes.

In a composition of the invention, such as in a coated or a coated and cross-linked coating composition of the invention, the level of retained enzymatic activity upon incubation in 84 mM HCl and 3.2 mg/ml pepsin at pH>1, e.g. in a range of pH about 1 to pH about 5, from pH about 2 to pH about 5, from pH about 2.5 to pH about 4.5, from pH about 2.5 to pH about 3.5 such as pH about 3, at 37° C. for at least 60 minutes, for at least for at least 80 minutes, for at least 100 minutes, for at least 120 minutes, for at least 140 minutes, for at least 160 minutes, for at least 180 minutes, for at least 200 minutes, for at least 220 minutes, for at least 220 minutes, or at for least 240 minutes, is increased by a factor of at least 2, at least 10, at least 50 or at least 100 as compared to compositions of enzymes of the same batch embedded in particles but where the particles lack a second layer of polymeric material (a coating), or a second layer that is cross-linked, or compared to the same batch of free enzymes.

As seen from the Examples herein, a composition of the invention wherein the bonds between the chemical cross-linking agent and the one or more enzymes and/or the first polymeric material and/or the second polymeric material have been reduced by a reducing agent, may lead to further improvements with respect to retaining the enzymatic activity of the composition. Such a reducing agent may be one well-known in the art such as e.g., a reducing agent such as $NaBH_4$ or $NaCNBH_3$.

In a composition of the invention, notably in a coated, with cross-linked coating, and reduced cross-links composition of the invention, wherein the first and/or second polymeric material may be cross-linked, and such a cross-linked material may or may not be reduced, the level of retained enzymatic activity upon incubation in 84 mM HCl and 3.2 mg/ml pepsin at pH>1, e.g. in a range of pH about 1 to pH about 5, from pH about 2 to pH about 5, from pH about 2.5 to pH about 4.5, from pH about 2.5 to pH about 3.5, such as pH about 3, at 37° C. for at least 60 minutes, for at least for at least 80 minutes, for at least 100 minutes, for at least 120 minutes, for at least 140 minutes, for at least 160 minutes, for at least 180 minutes, for at least 200 minutes, for at least 220 minutes, or for at least 240 minutes is increased by a factor of at least 2, at least 10, at least 50 or at least 100 as compared to compositions of the same batch of enzymes in a particle that has not been subjected to a reducing agent; or compared to the same batch of free enzymes.

In a specific embodiment of the invention, the one or more embedded enzymes retain at least two times, at least 10 times, at least 50 times or at least 100 times, the activity of the one or more non-embedded free enzymes obtained from the same batch of enzymes upon incubation in 84 mM HCl and 3.2 mg/ml pepsin at pH>1, e.g. in a range of pH about 1 to pH about 5, from pH about 2 to pH about 5, from pH about 2.5 to pH about 4.5, from pH about 2.5 to pH about 3.5, such as pH about 3, at 37° C. for at least 60 minutes, for at least 80 minutes, for at least 100 minutes, for at least 120 minutes, for at least 140 minutes, for at least 160 minutes, for at least 180 minutes, for at least 200 minutes, for at least 220 minutes, or for at least 240 minutes.

In another specific embodiment of the invention, the one or more embedded enzymes retain at least 50%, at least 60%, at least 70%, at least 80%, at least 90%, at least 95% of the initial activity of the embedded enzymes upon incubation in 84 mM HCl and 3.2 mg/ml pepsin at pH>1, e.g. in a range of pH about 1 to pH about 5, from pH about 2 to pH about 5, from pH about 2.5 to pH about 4.5, from pH about 2.5 to pH about 3.5, such as pH about 3, at 37° C. for at least 60 minutes, for at least 80 minutes, for at least 100 minutes, for at least 120 minutes, for at least 140 minutes, for at least 160 minutes, for at least 180 minutes, for at least 200 minutes, for at least 220 minutes, or for at least 240 minutes.

In a further specific embodiment of the invention, the one or more enzymes retain from about 95% to about 100% of the initial activity of the embedded enzymes upon incubation in 84 mM HCl and 3.2 mg/ml pepsin at pH>1, e.g. in a range of pH about 1 to pH about 5, from pH about 2 to pH about 5, from pH about 2.5 to pH about 4.5, from pH about 2.5 to pH about 3.5, such as pH about 3, at 37° C. for at least 60 minutes, for at least 80 minutes, for at least 100 minutes, for at least 120 minutes, for at least 140 minutes, for at least 160 minutes, for at least 180 minutes, for at least 200 minutes, for at least 220 minutes, or for at least 240 minutes.

The enzyme embedded in a particle of the invention is capable of reducing oxalate content of food. As demonstrated in the Examples herein, a composition of the invention comprising 20 mg of one or more oxalate-degrading enzymes degrades at least 40%, such as, e.g., at least 50%, at least 60%, at least 70%, at least 80%, at least 95% or at least 99% of the oxalate present in 200 g spinach within 1 hour at pH=2.5.

Compositions of the invention may be prepared by employment of various polymeric materials. The following notation is used in the examples herein:

OxDc XX nanoparticles, such as chitosan nanoparticles, denote nanoparticles wherein chitosan is employed as the first polymeric material in which OxDc is embedded.

YY coated OxDc XX microparticles, such as alginate coated OxDc chitosan nanoparticles, denote nanoparticles wherein chitosan is employed as the first polymeric material in which OxDc is embedded and the nanoparticles are coated with alginate.

ZZ cross-linked YY coated OxDc XX microparticles, such as glutaraldehyde cross-linked alginate coated OxDc chitosan microparticles, denote microparticles wherein chitosan is employed as the first polymeric material in which OxDc is embedded, and the nanoparticles are coated with alginate to form microparticles, and the microparticles are subsequently cross-linked with glutaraldehyde.

Reduced ZZ cross-linked YY coated OxDc XX microparticles, such as reduced glutaraldehyde cross-linked alginate coated OxDc chitosan microparticles, denote microparticles wherein chitosan is employed as the first polymeric material in which OxDc is embedded and the nanoparticles that are formed are coated with alginate, which forms microparticles, and the microparticles are subsequently cross-linked with glutaraldehyde and subjected to reduction.

Accordingly,

OxDc chitosan/TPP nanoparticles are nanoparticles made from chitosan which contain TPP and have OxDC embedded therein.

Alginate coated OxDc chitosan/TPP microparticles are microparticles based on the nanoparticles formed from chitosan and TPP and embedded OxDc, the nanoparticles are coated with alginate to form microparticles.

Glutaraldehyde cross-linked alginate coated OxDc chitosan/TPP microparticles corresponds to the microparticles mentioned above, but the microparticles have been subjected to glutaraldehyde treatment to establish cross-linking.

Reduced glutaraldehyde cross-linked alginate coated OxDc chitosan/TPP microparticles corresponds to the microparticles mentioned above further being subjected to a reduction process.

A composition of the invention is suitable for use for oral administration to a subject. A composition is provided as oral pharmaceutical formulations, which may be delivered to the oral cavity, the mouth, a buccal patch, to the stomach, attached to the stomach mucosa, in a slow release liquid, in a quick release tablet in the mouth or stomach, coating the esophagus, in a liquid or solid form accompanying food, prior to ingesting food, or immediately after ingesting food.

The composition administered is normally in solid form e.g. in the form of particles or in a solid dosage form e.g. in the form of sachets, capsules or tablets (e.g. the particles are further processed into a suitable dosage form by methods well-known by a person skilled in the art). To this end, suitable pharmaceutically acceptable excipients may be added such as, e.g., fillers, binders, disintegrants, colors, flavors, pH-adjusting agents, stabilizers etc. Moreover, one or more further therapeutically and/or prophylactically substances may be added and/or other enzymes, cofactors, substrates, coenzymes, minerals and other agents that are helpful in the reduction of oxalate.

Examples of suitable pharmaceutically acceptable excipients include: dextrins, maltodextrins, dextrose, fructose, glucose, lactose, cellulose derivatives including carboxymethylcellulose calcium, carboxymethylcellulose sodium, hydroxypropylcellulose, hydroxypropylmethylcellulose (HPMC), microcrystalline cellulose (e.g., various grades of Avicel®), starches or modified starches (e.g. potato starch, maize starch, rice starch, pre-gelatinised starch), polyvinyl acetate, polyvinylpyrrolidone, agar, sodium alginate, sodium croscarmellose, calcium hydrogen phosphate, calcium phosphate (e.g. basic calcium phosphate, calcium hydrogen phosphate), calcium sulphate, carboxyalkylcellulose, dextrates, dibasic calcium phosphate, gelatine, gummi arabicum, hydroxypropyl cellulose, hydroxypropylmethylcellulose, methylcellulose, polyethylene glycol, polyethylene oxide, and as lubricants: talc, magnesium stearate, calcium stearate, stearic acid, hydrogenated vegetable oils and the like.

Methods of the present invention comprise treating or preventing oxalate-related conditions in humans and animals by administering an effective amount of oxalate-reducing compositions comprising one or more oxalate-reducing microorganisms, one or more oxalate reducing enzymes or combination and mixtures thereof in the particle compositions taught herein. Methods comprise providing compositions comprising the enzyme-embedded particles taught herein to a subject, human or animal, and reducing oxalate present in the subject, treating or preventing oxalate related conditions, and/or reducing a portion of the oxalate ingested. Methods for reducing oxalate in a human or animal comprise administering an effective amount of a composition comprising one or more oxalate-reducing enzymes or fragments having oxalate reducing activity in the embedded enzyme particle compositions of the present invention to a subject, human or animal, and reducing oxalate present. The reduction may take place in any tissue or body fluid environment of the subject. Body fluids include secretions of the body such as nasal or gastric secretions, saliva, blood, serum, urine, chyme or digestive matter, tissue fluid, and other fluid or semi-solid materials made by humans or animals. For example, embedded enzyme particle compositions can be administered orally to a human or animal and the oxalate-reducing enzyme activity reduces the oxalate present in the stomach of the human or animal. Embedded enzyme particle compositions of the present invention may be mixed in liquids, food or other dietary materials and provided to a human or animal so that the oxalate-reducing enzyme activity of the particles is effective in the stomach environment. Embedded enzyme particle compositions of the present invention may also be mixed with foodstuffs or other materials in which oxalate is found and the oxalate-reducing enzyme activity of the particles reduces the oxalate present in the foodstuff or other materials.

The methods for treating and preventing oxalate-related conditions comprise administering a composition comprising particles comprising an effective amount of oxalate-reducing enzymes. An effective amount comprises an amount of activity units of oxalate-reducing enzyme activity that will reduce a portion of the oxalate present, or a level of activity units of oxalate-reducing enzyme activity that will initiate a reduction in the amount of oxalate or maintain a lowered amount of oxalate in the individual compared to the amount of oxalate present before administration of the composition. The number of activity units of oxalate-reducing enzyme activity that can be used in a single dose composition can range from about 0.0001 units to about 5,000 units, from about 5 units to 100 units, from 0.05 to 50 units, to 0.5 to 500, from about 0.01 units to about 50 units, from about 0.01 units to about 5 units, from about 1 units to about 100 units, from about 25 units to about 50 units, from about 30 units to about 100 units, from about 40 units to about 120 units, from about 60 units to about 15 from about 50 units to about 100 units, from about 100 units to about 500 units, from about 100 units to about 300 units, from about 100 units to about 400 units, from about 100 units to about 5,000 units, from about 1,000 units to about 5,000 units, from about 2,500 units to about 5,000 units, from about 0.001 units to about 2,000 units and all ranges encompassed therein. The compositions may further include other enzymes, cofactors, substrates, coenzymes, minerals and other agents that are helpful in the reduction of oxalate. An unit of the enzyme is the amount of enzyme that will degrade one micromole of oxalate per minute at 37° C.

In a treatment method, an effective amount of a particle composition as taught herein is administered orally to be ingested by a subject at least once a day, at least twice a day, at least three times a day, at least four times a day or more if necessary, and such administration can be for one day, two days, three days, four days, five days, or a week, two weeks, three weeks, or a month, two months, three months, four months, five months, six months, more than six months, one year, two years, or for years or continuously through the life of the patient. Such treatment may be continued to maintain the desired oxalate levels in a subject.

It must be noted that, as used in this specification and the appended claims, the singular forms "a", "an", and "the" include plural referents unless the context clearly dictates otherwise.

All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention are provided herein, the present invention is not limited to these embodiments. There are numerous modifications or alterations that may suggest themselves to those skilled in the art.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Methods

Assay for Enzymatic Activity

Samples are appropriately diluted with Tris buffer (typically 5 or 10 times) to 0.5-1 mg/ml, of which 10 µL are aliquoted into 1.5 mL eppendorf tubes. To each tube, 390 µL warm substrate buffer (usually 20 mM oxalate in 20 mM citrate buffer, pH 4) is added and immediately placed on a thermomixer for exactly 10 minutes, at which time 100 µL 0.5M $H_2SO_4$ is added. Total formate produced is measured directly by HPLC. Using an ion exchange column (Aminex HPX-87H, BioRad) and an isocratic gradient of 20 mM $H_2SO_4$, formate is detected by UV at 210 nm with peaks typically eluting at 14.3 minutes.

Stability Test

Incubation in Buffer at a pH of from About 2 to About 3

After incubation of OxDc free enzyme or the composition in question containing the OxDc enzyme embedded in a polymeric material in 100 mM glycine buffer at a pH range from 2 to 3 for a certain period, the remaining OxDc activity was analyzed.

Incubation in Simulated Gastric Fluid

A particle composition containing from about 2 mg OxDc to about 20 mg OxDc was placed in a vessel containing 100 mL of simulated gastric fluid prepared according to USP, i.e. by dissolving 2 g NaCl, 3.2 g pepsin, and 7 mL concentrated HCl in a final volume of 1 L. At suitable time intervals, a sample was drawn and assayed for OxDc activity as described above.

Incubation in Buffer

The same procedure as described above (for simulated gastric fluid). However, various buffer solutions were employed dependent on the pH value of interest. Suitable buffers include glycine buffers (pH 2-3), acetate buffers (pH 3-6), phosphate buffers (pH 5-8), borate buffers (pH 8-9) and the like. A protease may be added such as, e.g., pepsin in a concentration normally corresponding to the concentration found in the USP simulated gastric fluid.

Example 1

Preparation of OxDc Alginate Microparticles and Influence of Various Process Parameters on the Stability This example illustrates the preparation and stability of OxDc alginate microparticles and, furthermore, illustrates the influence of various process parameters on the stability of OxDc embedded in the microparticles.

Preparation of OxDc Alginate Microparticles

Microparticles I—Emulsification 1:

11 ml of the mixture of alginate (1.8%, w/v) and OxDc (10:1, v/v; OxDc, 20 mg/ml, in 10 mM TrisHCl, pH 3.9) in 50 mM citrate buffer, pH 3.9, were mixed with 20 ml mineral oil containing 0.5% triton x-100 by magnetic stirring at 600 rpm for 10 min to reach stable emulsion state, then 4 ml $CaCl_2$ mineral oil emulsion (2 ml 0.2 M $CaCl_2$+2 ml mineral oil) was added and continued to stir for 30 min. 8 ml chitosan mineral oil emulsion (4 ml 0.8% chitosan and 4 ml mineral oil) was then added and stirred for another 30 min. Microparticles were collected by centrifugation. In the following these microparticles are denoted Microparticles I.

Microparticles II—Emulsification 2:

All the same as "Emulsification 1" except that the mixture of alginate and OxDc was in 10 mM TrisHCl buffer, pH 8. In the following these microparticles are denoted Microparticles II.

Chitosan Coated OxDc Alginate Microparticles—Alginate Gelation at Different Concentrations (Emulsification) and Further Coating of the Microparticles with Chitosan:

8 ml of alginate (1.2% or 3%; w/v) was mixed with 0.5 ml OxDc (16 mg/ml) in 50 mM TrisHCl buffer, pH 9, then mixed with 15 ml mineral oil containing 0.8% triton x-100 by magnetic stirring at 600 rpm for 10 min to reach stable emulsion state, then 8 ml $CaCl_2$ mineral oil emulsion (4 ml 1 M CaCl$_2$+4 ml mineral oil) was added and continued to stir for 30 min, then added 50 ml 1 M CaCl$_2$ under stirring. Microparticles were collected by centrifugation and washed with water twice. All microparticles (about 4 ml) were merged in the mixture of 36 ml 0.4% chitosan, pH 5.45 and 4 ml of 4 M CaCl$_2$ and shaken at 200 rpm for 1 h. In the following these microparticles are denoted as Chitosan coated OxDc alginate microparticles.

All microparticles obtained in this example had a particle size distribution estimated to be in a range of about 1-100 µm.

The microparticles obtained were assayed for enzymatic activity as described above. The total enzyme activity is the enzyme activity of the enzymes prior to embedding the enzymes in the polymeric matrix, and this amount is set to 100%. The following results were obtained:

About 40% and 48% of the total enzyme activity was found in the microparticles prepared at pH 3.9 (Microparticles I) and at pH 8 (Microparticles II), respectively. The stability of the two kinds of microparticles was tested at pH 3 with 3.2 mg/ml of pepsin.

Figure 2:
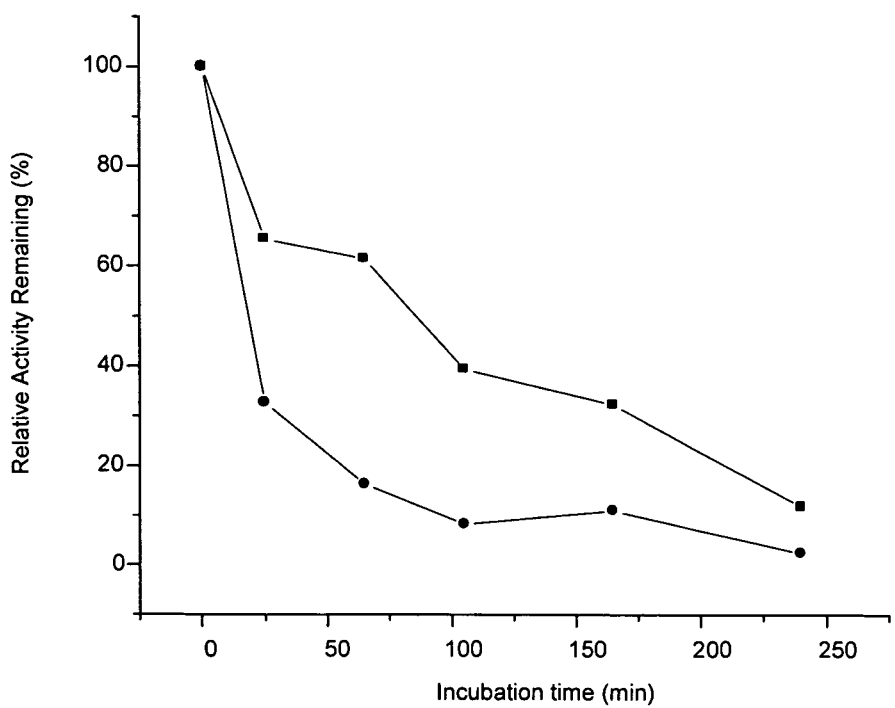
FIG. 2 is a graph which shows the effects of alginate concentration for forming alginate microparticles on the stability of OxDc in the chitosan coated OxDc alginate microparticles at pH 3 with pepsin.

About 42% and 60% of the total enzyme activity was found in the chitosan coated OxDc alginate microparticles prepared by 1.2% and 3% of alginate, respectively. The stability of the two kinds of chitosan coated OxDc alginate microparticles was tested at pH 3 with 3.2 mg/ml of pepsin (FIG. 2).

FIG. 1 is a graph of the stability of OxDc in the microparticles I (prepared at pH 3.9) and in the microparticles II (prepared at pH 8) under pH 3 with pepsin. Squares are microparticles I, triangles are microparticles II. FIG. 2 is a graph showing the effects of alginate concentration for forming alginate microparticles on the stability of OxDc in the chitosan coated OxDc alginate microparticles at pH 3 with pepsin. Squares are microparticles formed with 3% alginate, solid circles are microparticles formed with 1.2% alginate.

Accordingly, the pH present during the preparation of the microparticles seems to influence the stability of OxDc during incubation, i.e. an increase in pH favors better stability and an increase in alginate concentration also seems to have a positive impact on the stability.

Example 2

Preparation of OxDc Nanoparticles and Coating Thereof

This example illustrates the preparation of OxDc-containing nanoparticles and various coatings thereof.

OxDc Chitosan/tripolyphosphate Nanoparticles:

40 ml 0.15% (w/v) of tripolyphosphate (TPP) containing 0.5 mg/ml OxDC, pH 8.1 (adjusted by HCl before adding OxDC) was dropped into 120 ml 0.18% (w/v) chitosan in 0.13% (w/v) acetic acid, pH 3.92. Nanoparticles were collected by centrifugation and washed with water twice. This process produced about 4 ml of nanoparticles suspension.

Figure 3:
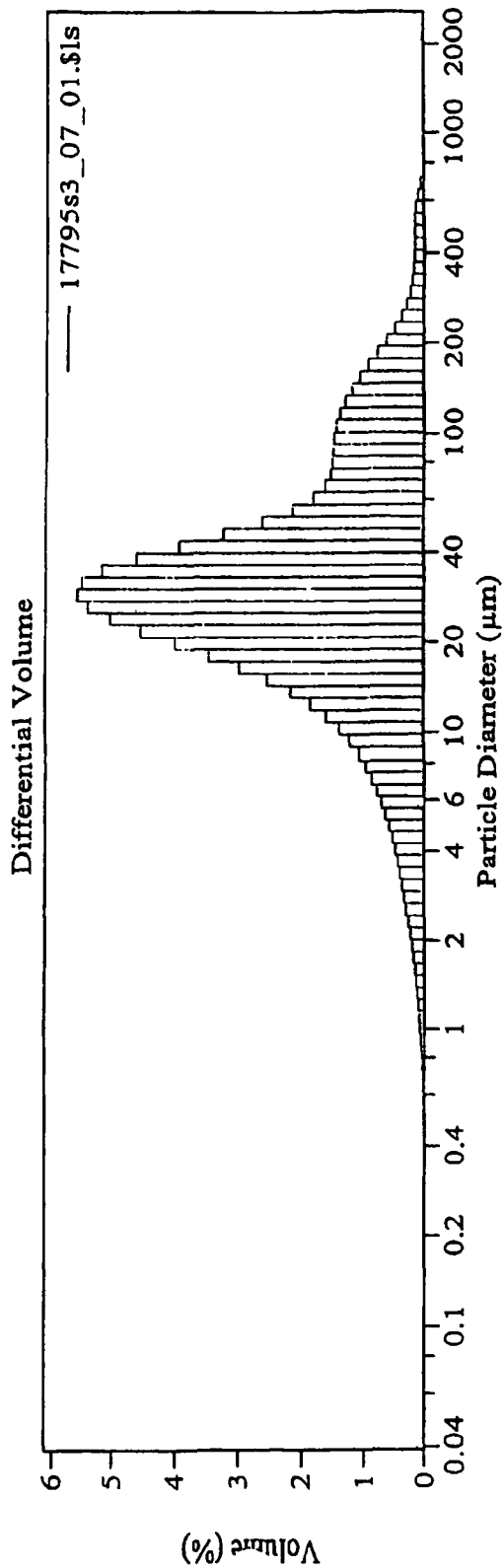
FIG. 3 is a graph showing particle size distribution of particles prepared according to Example 2 herein.

OxDc Chitosan/TPP Nanoparticles Coated with Alginate:

0.8 ml of the nanoparticle suspension was diluted in 10 ml water under stirring, and then 5 ml of 1.2% alginate solution (in 25 mM TrisHCl buffer, pH 8.6) was added by dropping. The mixture was kept under stirring for 5 min. The size of the coated nanoparticles increased to 2-400 µm, with the majority around 30 µm (see FIG. 3), because of aggregation of nanoparticles and crosslinking by alginate. The microparticles were collected by centrifugation at 3000 g for 3 min. The microparticles were washed with water twice and resuspended. In FIG. 3 the volume statistics (Arithmetic) 17795s3_07_01.$1s. Calculations from 0.040 µm to 2000 µm. Volume: 100%; Mean: 48.53 µm; Median: 29.10 µm; Mean/Median ratio: 1.668; Mode: 28.70 µm; S.D.: 65.43 µm; C.V. 135%; Skewness: 4.384 Right skewed; Kurtosis 26.90 Leptokurtic; $d_{10}$ 8.814 µm; $d_{50}$ 29.10 µm; $d_{90}$ 109.9 µm.

OxDc Chitosan/TPP Nanoparticles Coated with Carrageenen:

0.8 ml of the nanoparticle suspension was diluted in 10 ml water under stirring, then 5 ml of 0.5% carrageenen solution (natural pH 8.9) was added by dropping. The mixture was kept under stirring for 5 min. The coated nanoparticles should form microparticles and have a similar distribution as those coated with alginate (see above). The microparticles were collected by centrifugation and washed twice with water, and resuspended.

OxDc Chitosan/TPP Microparticles Coated with Either Alginate or Carrageenen Were Cross-linked with Glutaraldehyde at Different Concentrations of Glutaraldehyde:

0.2 ml of the microparticle suspension was diluted in 0.8 ml water under stirring, and then 2 ml of 0.15-7.5% glutaraldehyde solution (in 50 mM KPB, pH 7.5) was added and mixed. The mixture was kept under stirring for 15-40 min and the microparticles were collected by centrifugation and washed twice with water.

Reduction of Glutaraldehyde Cross-linked Alginate Coated OxDc Chitosan/TPP Microparticles Two different kinds of glutaraldehyde cross-linked alginate coated OxDc chitosan/TPP microparticles were prepared: one was cross-linked without addition of CaCl$_2$ and the other with addition of 1.2 M CaCl$_2$ 10 min after cross-linking reaction (1% of glutaraldehyde) started. After the cross-linking reaction ran for 1 h, microparticles were collected by centrifugation and washed with water twice. The two kinds of microparticles were further suspended in 100 mM of KPB, pH 7.5. A certain amount of NaBH$_4$ powder was added to the suspension solutions to make final concentration of 20 mM NaBH$_4$ and kept in the dark and shaking for 14 h.

The following results were obtained:

OxDc Chitosan/TPP Nanoparticles:

Nanoparticles were too small to be visually observed under the optical microscope. OxDc was almost 100% trapped by the nanoparticles under the current conditions. Under these conditions, OxDC was dissolved with TPP at high pH (8.6) and then dropped into a low pH (3.92) chitosan solution. The great preference of the enzyme dissolved in high pH over low pH is a factor in maintaining the enzyme inside the nanoparticles at the nanoparticle formation period. The stability of OxDc at pH 3.0 in the OxDc chitosan/TPP nanoparticles was between that of microparticle I and microparticle II from Example 1 and FIG. 1.

Figure 4:
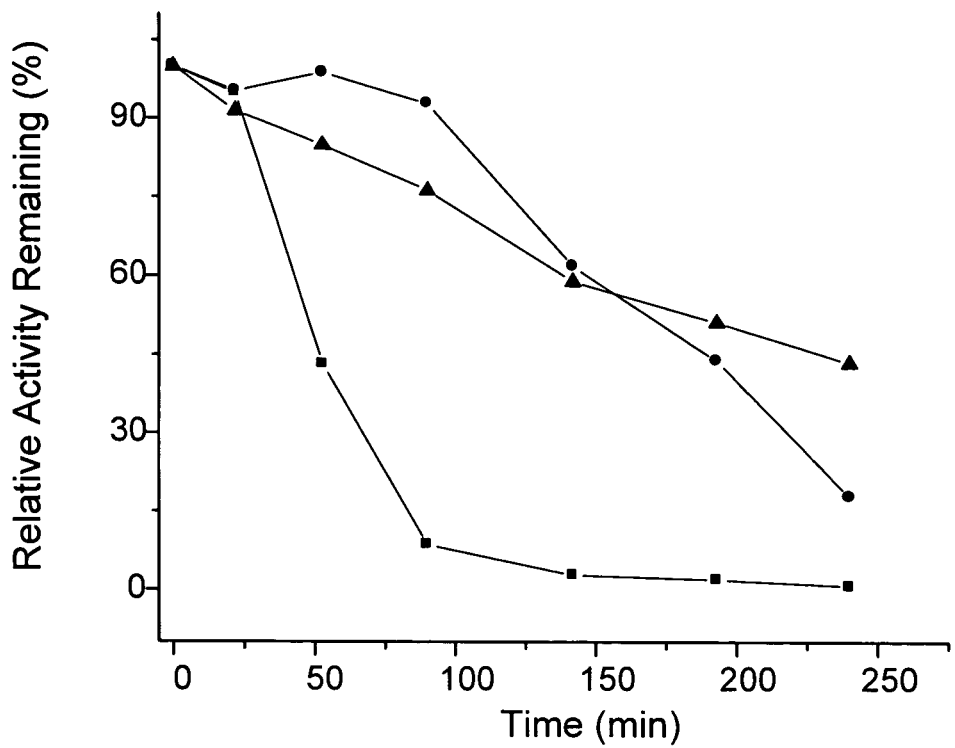
FIG. 4 is a graph which shows the effects of coating with alginate or carrageenen on the stability of OxDC in chitosan/TPP nanoparticles at pH 3 with pepsin.

Alginate Coated OxDC Chitosan/TPP Microparticles:

The stability of OxDc at pH 3.0 was further improved when an alginate coating was applied, compared to uncoated nanoparticles See FIG. 4, where squares are nanoparticles with no coating, closed circles are microparticles with alginate coating, and triangles are microparticles with carrageenen coating.

Carrageenen Coated OxDc Chitosan/TPP Microparticles:

The stability of OxDC at pH 3.0 was further improved when a carrageenen coating was applied (compared to uncoated nanoparticles) FIG. 4

Alginate Coated OxDc Chitosan/TPP Microparticles wherein the Whole Particle is Cross-linked with Glutaraldehyde at Different Concentrations of Glutaraldehyde:

(Though not wishing to be bound by any theory, it is believed that the glutaralaldehyde cross-linking occurs mostly within the chitosan molecule, linking chitosan molecules to itself and each other, and among chitosan molecules and enzyme molecules.)

Figure 5:
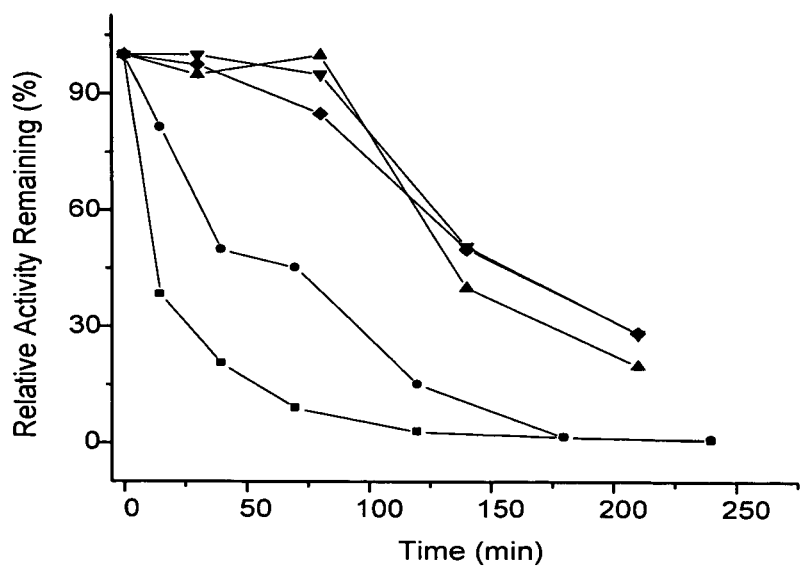
FIG. 5 is a graph showing the effects of glutaraldehyde concentrations for cross-linking on the stability of OxDc in the glutaraldehyde cross-linked alginate coated OxDc chitosan/TPP microparticles at pH 2.4 with pepsin.

Alginate coated microparticles plus cross-linking showed higher stability at low pH than the nanoparticles without alginate coating. High level of cross-linking improved the OxDc stability inside the alginate coated microparticles at low pH (FIG. 5). The most stable microparticles can be submerged in a solution at pH 2.6 with pepsin for 4 h without losing activity. The activity was about 30% after 3.5 h incubation at pH 2.4 with pepsin. See FIG. 5 which shows the effects of glutaraldehyde concentration for cross-linking on the stability of OxDc in the glutaraldehyde cross-linked alginate coated OxDc chitosan/TPP microparticles at pH 2.4 with pepsin. The squares are 1% glutaraldehyde with no alginate coating, solid circles are 0.5% glutaraldehyde, triangles pointing up are 1% glutaraldehyde, and triangles pointing down are 2% glutaraldehyde, and diamonds are 5% glutaraldehyde.

Figure 6:
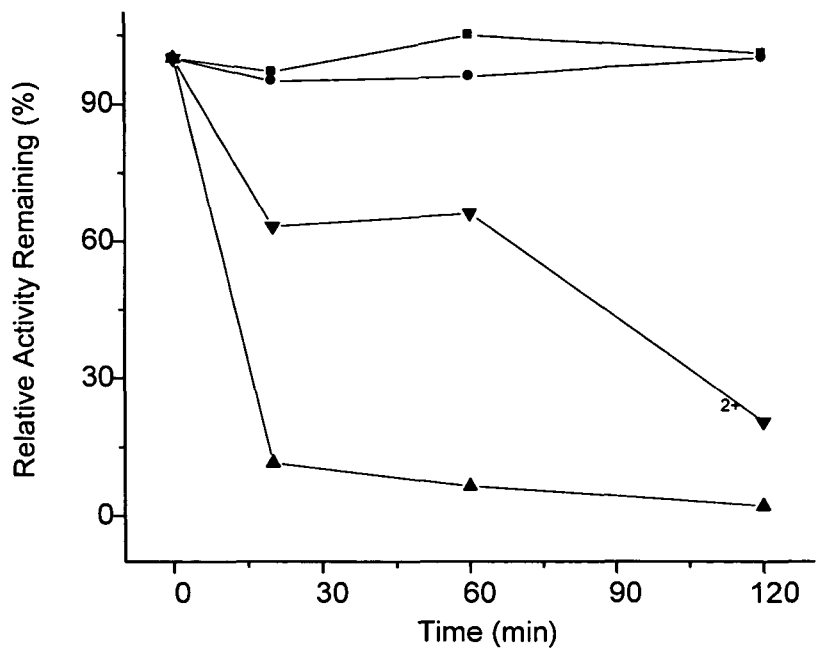
FIG. 6 is a graph which illustrates the stability of OxDc in two kinds of cross-linked and reduced microparticles under pH 2.2 and 1.85.

Reduction of Glutaraldehyde Cross-linked Alginate Coated OxDc Chitosan/TPP Microparticles:

The stability of the glutaraldehyde cross-linked alginate coated OxDc chitosan/TPP microparticles under low pH after the reduction of Schiff's double bounds was significantly improved. The glutaraldehyde cross-linked alginate coated OxDc chitosan/TPP microparticles with $CaCl_2$ addition during cross-linking lost 80% of OxDc activity after 120 minutes whereas the microparticles without $CaCl_2$ addition under pH around 2.0 lost 80% activity in a very short time. For details, see FIG. 6 which is a graph that shows the stability of OxDc in two kinds of cross-linked and reduced microparticles under pH 2.2 and 1.85, where the squares are pH 2.2, with no $Ca^{+2}$, solid circles are pH 2.2 with the addition of $Ca^{+2}$, triangles pointing up are pH 1.85 with no $Ca^{+2}$, and triangles pointing down are pH. 1.85 with $Ca^{+2}$.

From the above series of experiments, the formulation of reduced glutaraldehyde cross-linked alginate coated OxDc chitosan/TPP microparticles was selected for further development.

Example 3

Experiments for In Vitro Testing of Removing Oxalate from Food Under Simulated Stomach Condition In vitro testing of reduced glutaraldehyde cross-linked alginate coated OxDc chitosan/TPP microparticles 10, 20 and 40 g of spinach was mixed with 12 ml of simulated stomach juice (gastric fluid) (84 mM HCl with 3.2 mg/ml pepsin), respectively. Then water was added to make the final volumes of 40, 80 and 160 ml, respectively. After homogenizing the spinach, simulated gastric fluid and water, reduced glutaraldehyde cross-linked alginate coated OxDc chitosan/TPP microparticles were added to degrade the oxalate released from the spinach. The (dosage) ratio of spinach/microparticle is 200 (200 g of spinach mixed with 1 g of microparticles) for all three conditions. Spinach was selected for this experiment, because it contains high amount of oxalate (about 200 mM of oxalate in the frozen spinach leaf).

Figure 7:
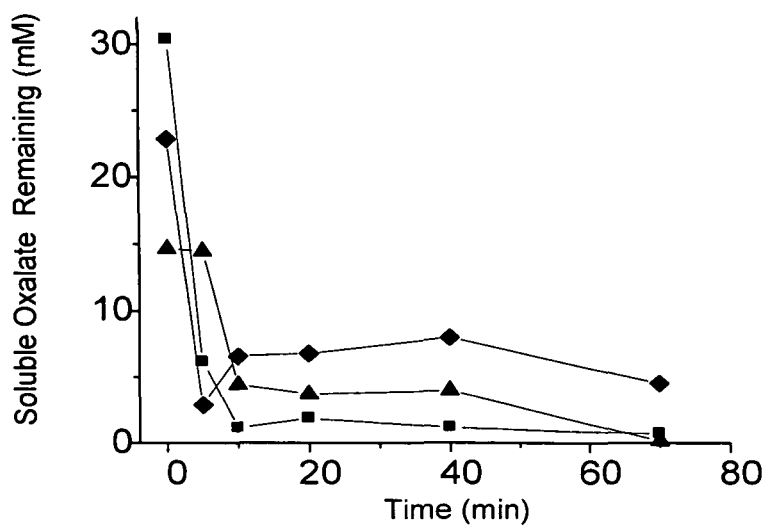
FIG. 7 is a graph showing the bioavailability of oxalate (soluble part) after administration of compositions of the invention.

Results and Discussion:

The amount of soluble oxalate is significantly influenced by pH. The pH values were 2.5, 3.5 and 4.2, for 10, 20 and 40 g of spinach conditions, respectively. The initial soluble oxalate concentrations were 30.0, 22.8 and 14.7 mM, for 10, 20 and 40 g of spinach conditions, respectively (FIG. 7). If all oxalate is soluble, its concentration should be around 48 mM. Thus, there was insoluble oxalate present under all three conditions. FIG. 7 indicates that the initial soluble oxalate was almost completely removed in a few minutes. The remaining soluble oxalate did not drop to 0, but remained at low level for a period, because insoluble oxalate started to dissolve when more soluble oxalate was removed. FIG. 7 shows the bioavailability of oxalate (soluble portion) was quickly reduced under all three conditions. The squares are 10 g of spinach with 0.05 g of washed microparticles, diamonds are 20 g of spinach with 0.1 g of washed microparticles, triangles pointing up are 40 g of spinach with 0.2 g of microparticles.

Figure 8:
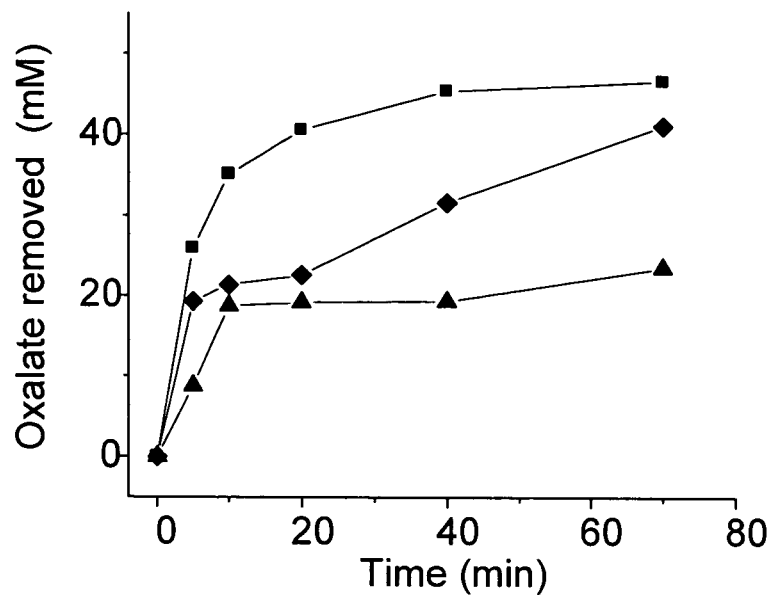
FIG. 8 is a graph which illustrates the time course of total soluble oxalate in spinach removed by microparticles in three different simulated conditions.

The OxDc microparticles kept removing more and more soluble oxalate (FIG. 8). After 1 h, almost all oxalate in spinach in the first condition (squares) and about 90% in the second condition (diamonds) was removed. For the third condition (triangles), only 50% oxalate was removed, but the soluble part was close to 0. Therefore, under all the three conditions, absorption of oxalate can also be effectively limited in GI tract, because the soluble oxalate concentration was very low and large part of oxalate was reduced. FIG. 8 is a graph of a timecourse of total soluble oxalate in spinach removed by microparticles in three different simulated conditions. The total oxalate concentrations in each of the spinach samples was about 50 mM. The squares are 10 g of spinach with 0.05 g of microparticles, diamonds are 20 g of spinach with 0.1 g of microparticles, triangles pointing up are 40 g of spinach with 0.2 g of microparticles.

If using these results to simulate treatment in vivo, assume that a person whose stomach contains 120 ml of gastric fluid is to begin ingesting a total of 400 g of spinach. After ingestion of 100 g spinach, 4 g of microparticles are taken. Almost all soluble oxalate will be removed within 2 min. Although ingestion of the spinach continues until 400 g is eaten, soluble oxalate is maintained below 3 mM during eating and quickly reduces to 0 after eating.

Example 4

Formulated OxDc According to the Invention

I. Preparation of Formulated OxDc (Microparticles) and Testing its Stability at Low pH Reduced glutaraldehyde cross-linked alginate coated OxDc chitosan/TPP microparticles are produced as follows:
1. OxDc chitosan/TPP nanoparticles formed by dropping tripolyphosphate (TPP) solution into a mixture of chitosan and OxDc.
2. Coating the above nanoparticles with alginate by addition of alginate solution to above suspension. The nanoparticles formed microparticles because of the aggregation of nanoparticles and physical crosslinking by alginate occurred during this process.
3. Cross-linking of above microparticles by glutaraldehyde
4. Reduction of Schiff's base by $NaBH_4$ The preparation was made in accordance with the description in Example 2.

Figure 9:
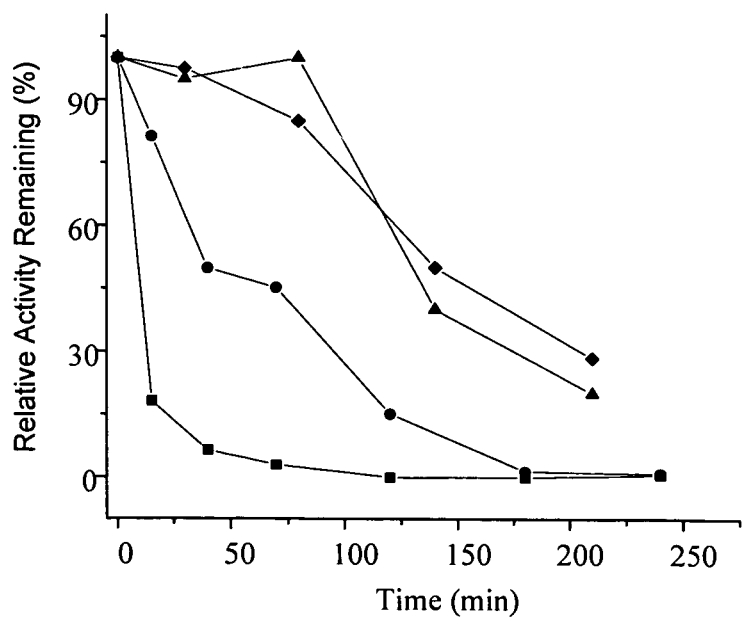
FIG. 9 is a graph that shows the effects of cross-linking with glutraldehyde (1-5%) in chitosan microparticles at pH 2.4 and in the presence of pepsin.

Testing the Stability of Free or Formulated OxDc at Low pH:

After incubation of OxDc as free enzyme or in this microparticle in 100 mM glycine buffer at a pH range from 2 to 3 for a certain period, the remained OxDc activity was analyzed. FIG. 9 is a graph showing the cross-linking with glutraldehyde (0.5-5%) improved the stability of OxDc in alginate coated chitosan/TPP microparticles at pH 2.4 and in the presence of pepsin. The squares are 0% glutaraldehyde, solid circles are 0.5% glutaraldehyde, triangles pointing up are 1% glutaraldehyde and diamonds are 5% glutaraldehyde.

Figure 10:
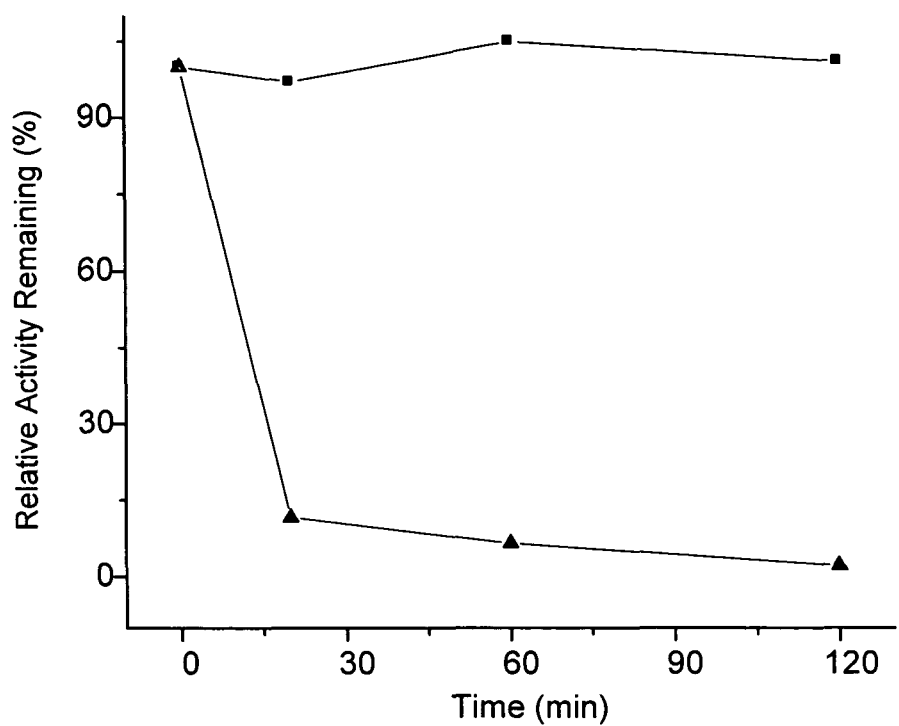
FIG. 10 is a graph illustrating reduction of Schiff's base in the glutaraldehyde cross-linked alginate coated OxDc chitosan/TTP microparticles at differing pHs and in the presence of pepsin.

As shown in FIG. 9, the activity of the alginate coated OxDc chitosan/TPP microparticles without cross-linking (control) represented by the square points is completely destroyed in less than 15 minutes at pH of 2.4. In contrast cross-linking with 0.5-5% of glutraldehyde stabilizes the enzyme activity of the alginate coated OxDc chitosan/TPP microparticles for up to 2 hours. Native (unformulated, free, non-embedded) OxDc is known to be irreversibly inactivated at pH<3.0. The stability of the glutaraldehyde crosslinked alginate coated OxDc chitosan/TPP microparticles was further improved after reduction of the Schiff's base in these microparticles (FIG. 10). FIG. 10 is a graph showing th reduction by Schiff's base improved the stability of OxDc in the glutaraldehyde cross-linked alginate coated OxDc chitosan/ TTP microparticles at pH 2.2 and in the presence of pepsin (square points). The microparticles are inactivated rapidly at pH<2.0 (triangle points).

Reduced glutaraldehyde cross-linked alginate coated OxDc chitosan/TTP microparticles retain stability at pH as low as 2.2. This is a significant improvement since the unformulated enzyme (free, non-embedded) is irreversibly inactivated at pH<3.0.

II. Studies on the Degradation of Oxalate by OxDc Microparticles

A. Degradation of Oxalate (as Sodium Oxalate) in Low Concentration Range:

OxDc microparticles (prepared as described under I, Example 4 above) containing 2 or 20 mg of OxDc were mixed with 100 ml oxalate solution with concentration from 0.05 to 2 mM at pH 3 at 37° C. The generated formate was measured during a period of time.

Figure 11:
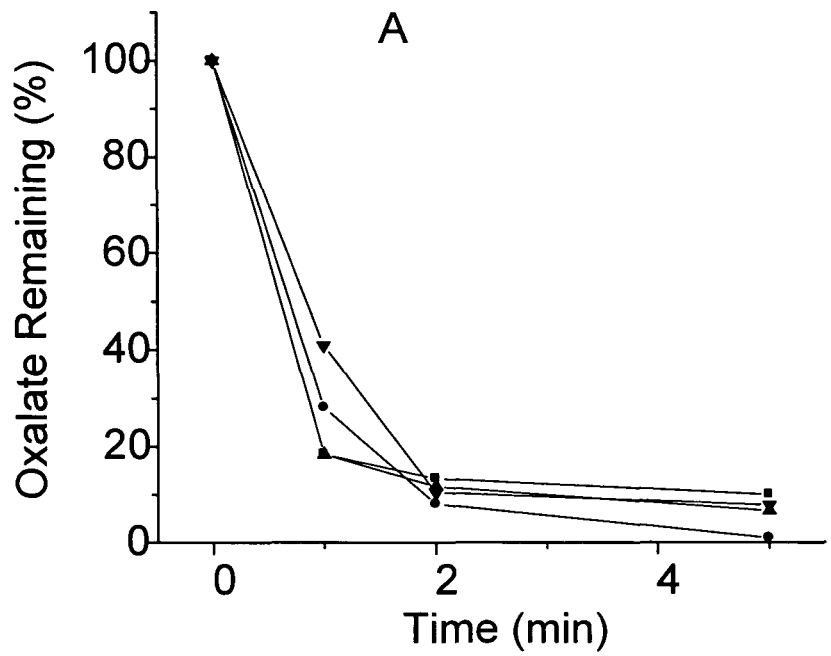
FIGS. 11A and B are graphs showing oxalate removed by reduced glutaraldehyde cross-linked alginate coated OxDc chitosan/TPP microparticles at pH 3.
Figure 11:
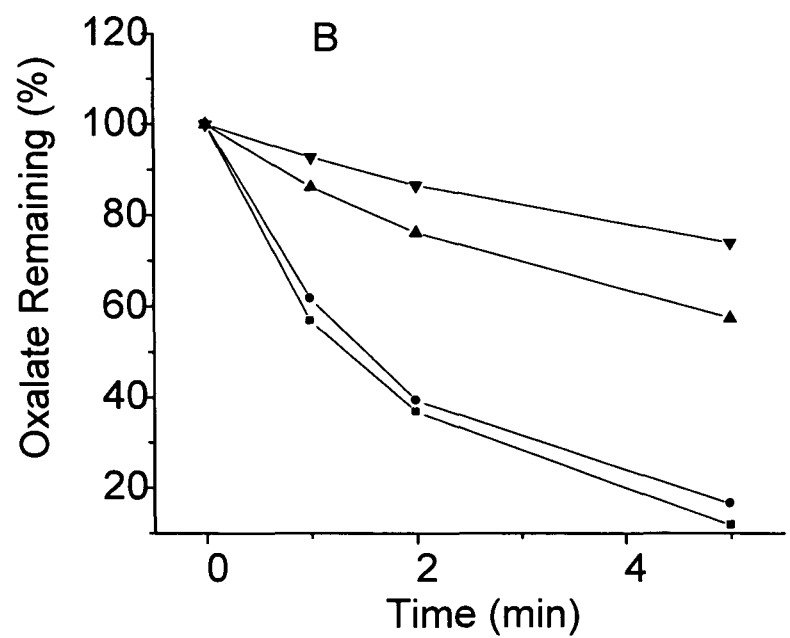

As shown in FIGS. 11A and B, the reduced glutaraldehyde cross-linked alginate coated OxDc chitosan/TTP microparticles can degrade oxalate at least in the concentrations ranging from 0.05 mM to 2.0 mM.

0.05 mM to 2 mM oxalate concentration in the human stomach corresponds to a dietary intake of 5 mg to 180 mg of oxalate and an assumed stomach volume of 1 L. The average daily intake of oxalate in the Western diet is reported to be 100-500 mg/day in all the meals. The intake can be much higher if some high oxalate foods like spinach are eaten. Degradation of oxalate in the range of 15 to 30 mM from spinach has also been investigated and is described below.

FIGS. 11A and B are graphs showing oxalate removed by reduced glutaraldehyde cross-linked alginate coated OxDc chitosan/TPP microparticles at pH 3. A, microparticles corresponding to 20 mg OxDc in 100 ml oxalate solution; B, microparticles corresponding to 2 mg OxDc in 100 ml oxalate solution. The squares are 0.05 mM oxalate concentration, solid circles are 0.2 mM oxalate concentration, triangles pointing up are 1.0 mM oxalate concentration, and triangles pointing down are 2.0 mM oxalate concentration.

20 mg of OxDc (estimated amount of enzyme protein in 1.0 ml of the microparticle formulation) almost completely degraded 0.05 mM to 2 mM oxalate in 2 minutes.

Degradation of Spinach Oxalate in Simulated Gastric Conditions:

Mixing spinach with simulated gastric fluid: 10, 20 and 40 g of spinach was mixed with 12 ml of simulated stomach juice (84 mM HCl with 3.2 mg/ml pepsin) then water was added to make the final volumes of 40, 80 and 160 ml, respectively.

Removing oxalate by OxDc: After homogenization of the spinach, gastric fluid and water suspensions, OxDc microparticles were added to degrade oxalate released from spinach. The (dosage) ratio of spinach/OxDc is approximately 2000 (2000 g of spinach mixed with microparticles having the activity of 1 g of OxDc) for all three conditions.

Figure 12:
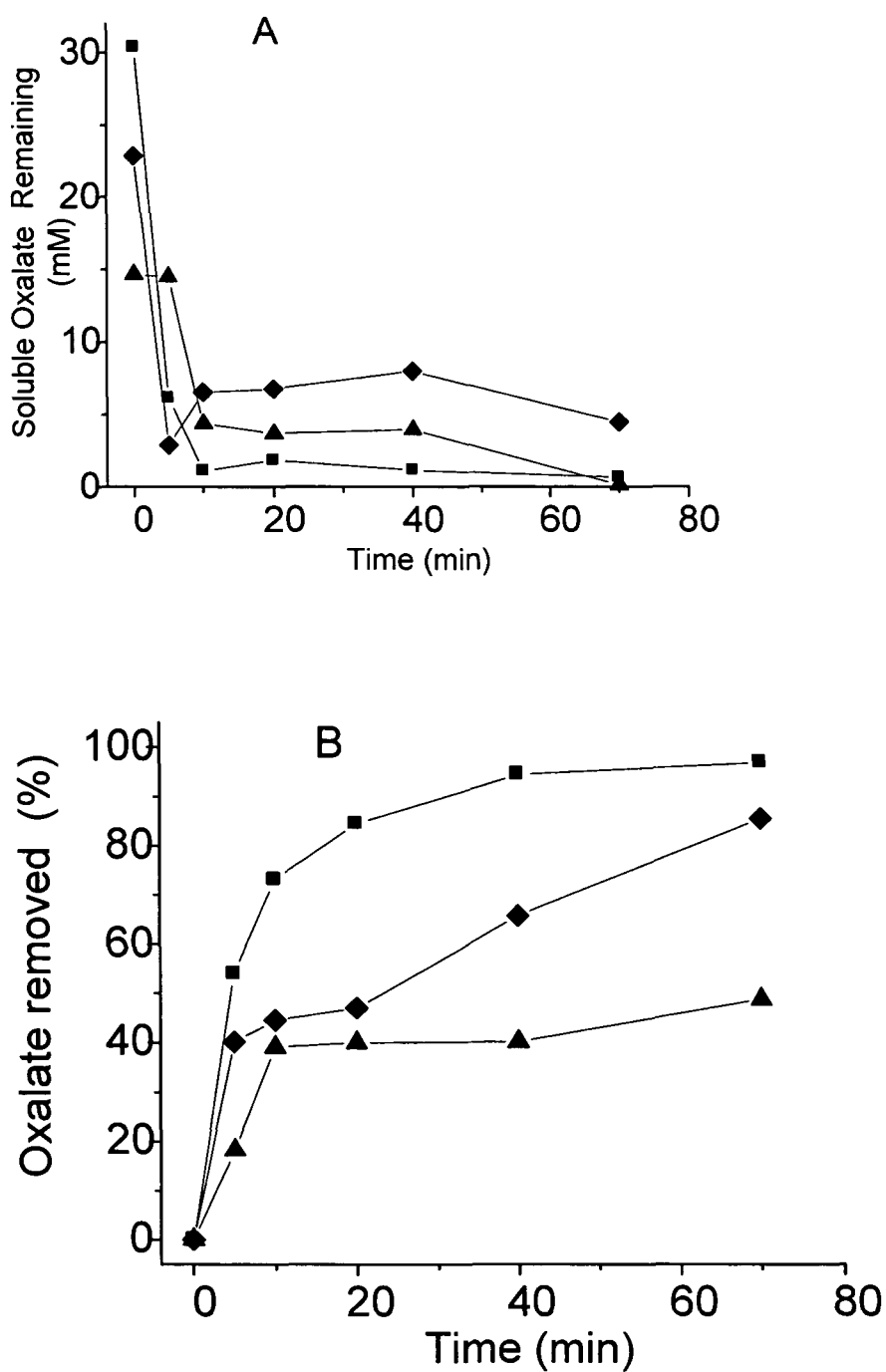
FIG. 12A is a graph that shows the bioavailability of oxalate (soluble part) after administration of compositions of the invention.
FIG. 12B is a graph illustrating the percentage of total oxalate removed.

Calculated total oxalate in all of the above preparations was 50 mM (spinach is reported to contain 18 g of total oxalate/ kg). Due to different levels of buffering of the gastric fluid by the presence of spinach, the final pH of three spinach suspensions was 2.5, 3.5 and 4.2, respectively. The pH of the medium is known to affect the availability of soluble oxalate and therefore the concentration of bioavailable oxalate in three preparations tested were 30 mM (square points), 22 mM (diamond points) and 15 mM (triangle points), respectively. (FIG. 12)

TABLE 1

| Spinach Preparations | pH | Total oxalate conc | Soluble oxalate conc |
|---|---|---|---|
| 10 g/40 ml gastric juice | 2.5 | 50 mM | 30 mM |
| 20 g/80 ml gastric juice | 3.5 | 50 mM | 22 mM |
| 40 g/160 ml gastric juice | 4.2 | 50 mM | 15 mM |

FIG. 12A is a graph showing the bioavailability of oxalate (soluble part) which was quickly reduced under all three conditions; 12B is a graph showing the percentage of total oxalate removed. The squares are 10 g of spinach with an amount of microparticles equal to 5 mg of OxDc (by enzymatic activity); diamonds are 20 g of spinach with an amount of microparticles equal to 10 mg of_OxDc, triangles pointing up are 40 g of spinach with an amount of microparticles equal to 20 mg of OxDc.

The microparticles with OxDc were capable of degrading a wide range of oxalate concentration from 0.05 mM to 30 mM in simulated gastric conditions in pH ranging from 2.5 to 4.2 (see FIGS. 12A and B) or in a buffer at pH 3 (FIGS. 11A and B). From this set of experiments it can be estimated that 20 mg of microparticles with OxDc (in 1.0 ml suspension) can degrade 180 mg of oxalate within 30 minutes.

What is claimed is:

1. An oral composition for degrading oxalate in the stomach comprising a coated particle comprising:
   a particle comprising an oxalate-degrading enzyme embedded in a first polymeric material that is permeable to oxalate in a pH range of from about 1 to about 5, wherein the first polymeric material is cross-linked to itself and/or to the enzyme, and
   a coating on the particle, wherein the coating comprises a second polymeric material that is permeable to oxalate in a pH range of from about 1 to about 5,
   wherein the second polymeric material is cross-linked to itself, to the first polymeric material, and/or to the embedded oxalate-degrading enzyme,
   wherein reducible bonds between a cross-linking agent and the embedded oxalate-degrading enzyme, the first polymeric material, and/or the second polymeric material have been reduced by a reducing agent.

2. The composition of claim 1, wherein the embedded oxalate-degrading enzyme retains at least about 30% of its initial activity when incubated in an aqueous buffer solution having a pH in the range of from about 1.0 to about 4.5 for 60 minutes.

3. The composition of claim 1, wherein the embedded oxalate-degrading enzyme retains at least about 20% of its initial activity when incubated in an aqueous buffer solution having a pH in the range of from about 1.0 to about 4.5 for 2 hours.

4. The composition of claim 2, wherein the buffer further comprises a protease.

5. The composition of claim 4, wherein the protease concentration is in a range of from about 0.5 mg/ml to about 10 mg/ml.

6. The composition of claim 1, wherein the oxalate-degrading enzyme comprises one or more selected from the group consisting of oxalate oxidase, oxalate decarboxylase, oxalyl-CoA decarboxylase, formyl-CoA transferase, and a combination of oxalyl-CoA decarboxylase and formyl-CoA transferase.

7. The composition of claim 6, wherein the oxalate-degrading enzyme comprises oxalate decarboxylase.

8. The composition of claim 1, wherein the embedded oxalate-degrading enzyme retains at least two times the oxalate-degrading activity as compared to a comparable non-embedded free oxalate-degrading enzyme from the same batch when incubated in 84 mM HCl and 3.2 mg/ml pepsin at pH>2 at 37° C. for at least 60 minutes.

9. The composition of claim 1, wherein the embedded oxalate-degrading enzyme retains at least two times the oxalate-degrading activity when incubated in 84 mM HCl and 3.2 mg/ml pepsin at pH>2 at 37° C. for at least 60 minutes as compared to the oxalate-degrading activity in a comparable composition wherein the first polymeric material is not cross-linked to itself or to the enzyme.

10. The composition of claim 1, wherein the reducing agent comprises $NaBH_4$ or $NaCNBH_3$.

11. The composition of claim 1, wherein the embedded oxalate-degrading enzyme retains at least two times the oxalate-degrading activity when incubated in 84 mM HCl and 3.2 mg/ml pepsin at pH>2 at 37° C. for at least 60 minutes as compared to the oxalate-degrading activity in a comparable composition that comprises a reducible cross-link which has not been subjected to the reducing agent.

12. The composition of claim 1, wherein the embedded oxalate-degrading enzyme retains at least about 50% of its initial activity when incubated in 84 mM HCl and 3.2 mg/ml pepsin at pH>1 and 37° C. for at least 60 minutes.

13. The composition of claim 1, wherein the first and/or second polymeric material are permeable to products of an oxalate-degradation reaction catalyzed by the embedded oxalate-degrading enzyme.

14. The composition of claim 1, wherein the coated particle has a diameter of from about 50 nm to about 1 mm.

15. The composition of claim 1, wherein the first and/or second polymeric materials remain substantially intact when incubated in 84 mM HCl and 3.2 mg/ml pepsin at pH>1 and 37° C. for at least 60 minutes.

16. The composition of claim 1, wherein the first and second polymeric materials are different.

17. The composition of claim 1, wherein the composition comprises about 2 mg to about 20 mg of the oxalate-degrading enzyme.

18. A method for degrading oxalate, comprising orally administering the composition of claim 1 to a subject in need of oxalate degradation.

* * * * *

UNITED STATES PATENT AND TRADEMARK OFFICE
CERTIFICATE OF CORRECTION

PATENT NO.           : 8,900,575 B2
APPLICATION NO.      : 11/640126
DATED                : December 2, 2014
INVENTOR(S)          : Qingshan Li et al.

It is certified that error appears in the above-identified patent and that said Letters Patent is hereby corrected as shown below:

On the title page

Item (75) Inventors:

Delete "Harmeet Sidhu, Gainesville, FL (US)" and insert -- Harmeet Sidhu, Atlanta, GA (US) --.

Signed and Sealed this
Twenty-ninth Day of December, 2015

Michelle K. Lee
*Director of the United States Patent and Trademark Office*